United States Patent
Dean et al.

(10) Patent No.: US 9,585,654 B2
(45) Date of Patent: Mar. 7, 2017

(54) SEGMENTALLY RIGID SUTURE AND SUTURING TECHNIQUE

(71) Applicant: Dean & Webb LLC, Austin, TX (US)

(72) Inventors: John C. Dean, Midland, TX (US); Jonathan H. Webb, Midland, TX (US)

(73) Assignee: Dean & Webb, LLC, Austin, TX (US)

( * ) Notice: Subject to any disclaimer, the term of this patent is extended or adjusted under 35 U.S.C. 154(b) by 674 days.

(21) Appl. No.: 13/874,243

(22) Filed: Apr. 30, 2013

(65) Prior Publication Data
US 2013/0296893 A1 Nov. 7, 2013

Related U.S. Application Data

(60) Provisional application No. 61/640,997, filed on May 1, 2012.

(51) Int. Cl.
*A61B 17/04* (2006.01)
*A61B 17/06* (2006.01)

(52) U.S. Cl.
CPC .... *A61B 17/06166* (2013.01); *A61B 17/0401* (2013.01); *A61B 17/0491* (2013.01); *A61B 17/0469* (2013.01); *A61B 2017/044* (2013.01); *A61B 2017/0406* (2013.01); *A61B 2017/0408* (2013.01); *A61B 2017/0414* (2013.01); *A61B 2017/0464* (2013.01); *A61B 2017/06176* (2013.01)

(58) Field of Classification Search
CPC .......... A61B 17/0401; A61B 17/06166; A61B 2017/06185; A61B 2017/0414; A61B 2017/06176; A61B 2017/0406; A61B 2017/0464
See application file for complete search history.

(56) References Cited

U.S. PATENT DOCUMENTS

| 4,516,584 A | 5/1985 | Garcia |
| 4,553,961 A | 11/1985 | Pohndorf et al. |

(Continued)

FOREIGN PATENT DOCUMENTS

| EP | 0218128 B1 | 12/1990 |
| EP | 0597213 B1 | 5/1994 |

(Continued)

OTHER PUBLICATIONS

International Search Report and Written Opinion in counterpart PCT Appl. PCT/US2013/038964, dated Aug. 2, 2013.

(Continued)

*Primary Examiner* — Ashley Fishback
(74) *Attorney, Agent, or Firm* — Blank Rome, LLP

(57) ABSTRACT

The suture device of the present disclosure disposes rigid components on suture, enabling the device to resist tensile and compressive loads and to protect soft tissue from suture pull-through. The suture device generally comprises of at least one rigid segment as well as a standard high tensile strength suture to create a segmentally rigid suture device. The at least one rigid segment may be comprised of any of a number of materials that are appropriate for use in the human body and provide the desired strength and stiffness for a particular application. Although the segmentally rigid suture device could be used with any prior art suture configuration, a grip stitch, a knot tying grip stitch, a straight-line grip stitch, and a reverse straight-line grip stitch suture configuration are described.

29 Claims, 32 Drawing Sheets

(56) References Cited

U.S. PATENT DOCUMENTS

| | | |
|---|---|---|
| 4,672,979 A | 6/1987 | Pohndorf |
| 5,107,856 A | 4/1992 | Kristiansen et al. |
| 5,152,298 A | 10/1992 | Kreyenhagen et al. |
| 5,242,431 A | 9/1993 | Kristiansen |
| 5,250,053 A | 10/1993 | Snyder |
| 5,383,904 A | 1/1995 | Totakura et al. |
| 5,423,763 A | 6/1995 | Helland et al. |
| 5,437,681 A | 8/1995 | Meade et al. |
| 5,476,493 A | 12/1995 | Muff |
| 5,603,730 A | 2/1997 | Romkee |
| 5,628,780 A | 5/1997 | Helland et al. |
| 5,645,568 A | 7/1997 | Chervitz et al. |
| 5,683,403 A | 11/1997 | Adams et al. |
| 5,683,446 A | 11/1997 | Gates |
| 5,707,394 A | 1/1998 | Miller et al. |
| 5,725,556 A | 3/1998 | Moser et al. |
| 5,746,722 A | 5/1998 | Pohndorf et al. |
| 5,824,032 A | 10/1998 | Belden et al. |
| 5,957,968 A | 9/1999 | Belden et al. |
| 6,027,523 A | 2/2000 | Schmieding |
| 6,613,059 B2 | 9/2003 | Schaller et al. |
| 6,921,407 B2 | 7/2005 | Nguyen et al. |
| 7,001,411 B1 | 2/2006 | Dean |
| 7,082,337 B2 | 7/2006 | Sommer et al. |
| 7,218,972 B2 | 5/2007 | Rodriguez |
| 7,242,986 B2 | 7/2007 | Rodriguez |
| 7,303,577 B1 | 12/2007 | Dean |
| 7,442,202 B2 | 10/2008 | Dreyfuss |
| 7,572,275 B2 | 8/2009 | Fallin et al. |
| 7,744,611 B2 | 6/2010 | Nguyen et al. |
| 7,831,313 B2 | 11/2010 | Lauro |
| 7,892,256 B2 | 2/2011 | Grafton et al. |
| 7,972,360 B2 | 7/2011 | Dean |
| 8,126,569 B2 | 2/2012 | Rivard et al. |
| 8,249,720 B2 | 8/2012 | Verzal et al. |
| 2003/0050668 A1 | 3/2003 | Lee |
| 2004/0059403 A1 | 3/2004 | Massullo |
| 2004/0254623 A1 | 12/2004 | Rodriguez et al. |
| 2007/0078399 A1 | 4/2007 | Olson |
| 2008/0255611 A1 | 10/2008 | Hunter |
| 2008/0281355 A1 | 11/2008 | Mayer et al. |
| 2009/0036905 A1 | 2/2009 | Schmieding |
| 2009/0125059 A1 | 5/2009 | Verzal et al. |
| 2009/0234386 A1 | 9/2009 | Dean et al. |
| 2010/0324569 A1 | 12/2010 | Helgesson |
| 2001/2030305 | 11/2012 | Huttunen et al. |
| 2013/0023930 A1 | 1/2013 | Stone et al. |

FOREIGN PATENT DOCUMENTS

| | | |
|---|---|---|
| EP | 0625359 A2 | 5/1994 |
| EP | 0824892 B1 | 7/1997 |
| EP | 0788770 A1 | 8/1997 |
| EP | 0957777 A1 | 11/1999 |
| EP | 1011788 B1 | 11/2003 |
| EP | 2263608 A1 | 12/2010 |
| EP | 2271393 A1 | 1/2011 |
| EP | 2497528 A1 | 9/2012 |
| EP | 2555689 A1 | 2/2013 |
| WO | 2009120116 A1 | 10/2009 |
| WO | 2011126588 A1 | 10/2011 |

OTHER PUBLICATIONS

Ponte, Brent A., et al., "Biomedical Evlauation of 3 Arthoscopic Self-Cinching Stitches for Shoulder Arthroscopy: The Lasso-Loop, Lasso-Mattress, and Double-Cinch Stitches," The American Journal of Sports Medicine 2011 39:188, originally published Nov. 12, 2010.

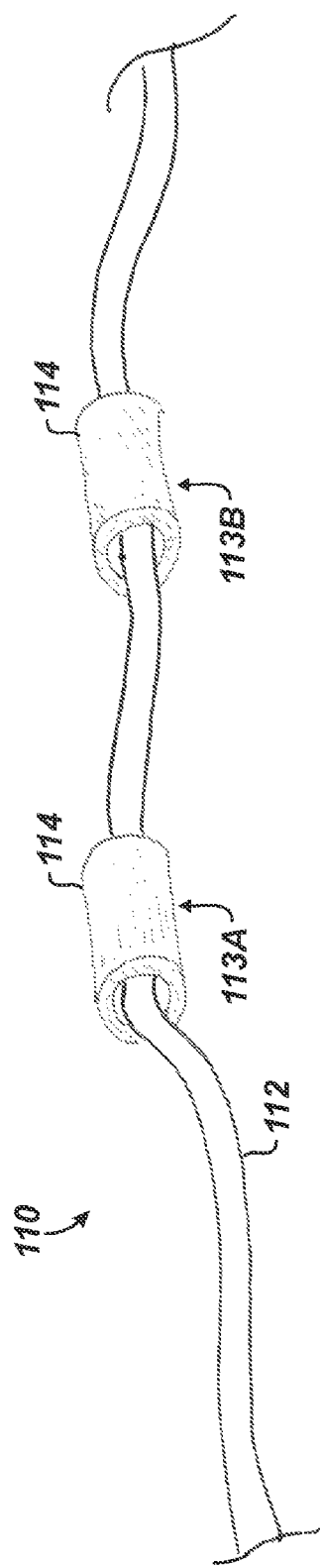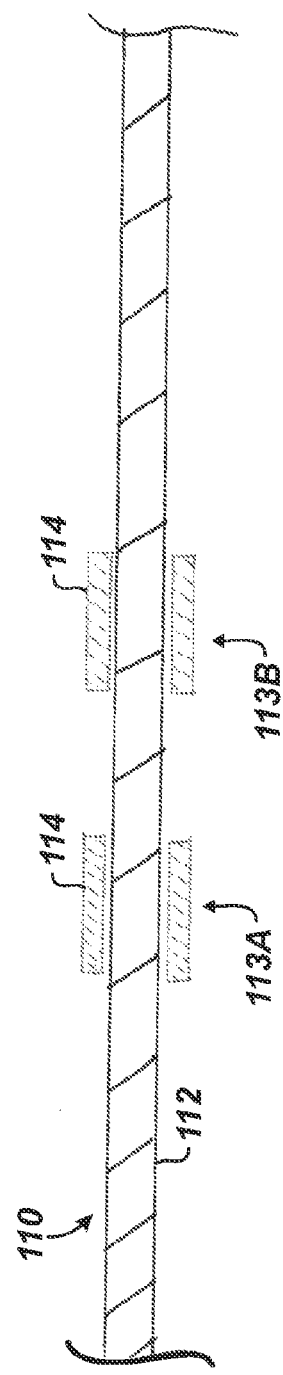

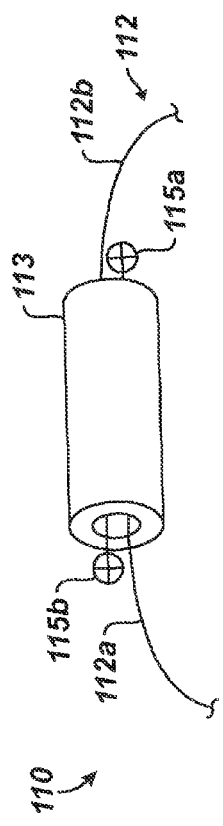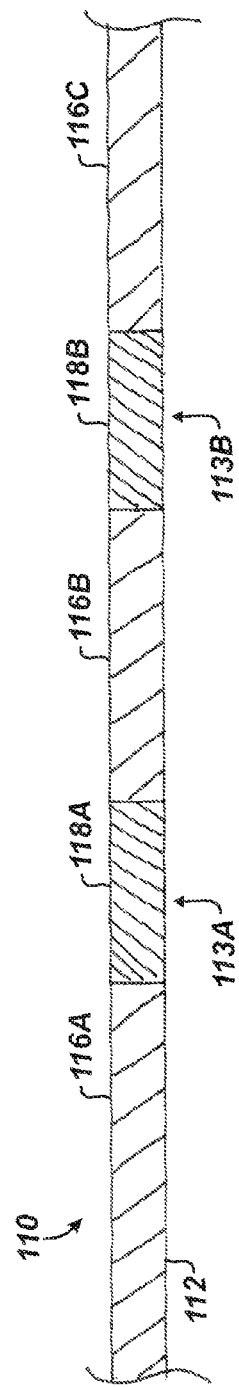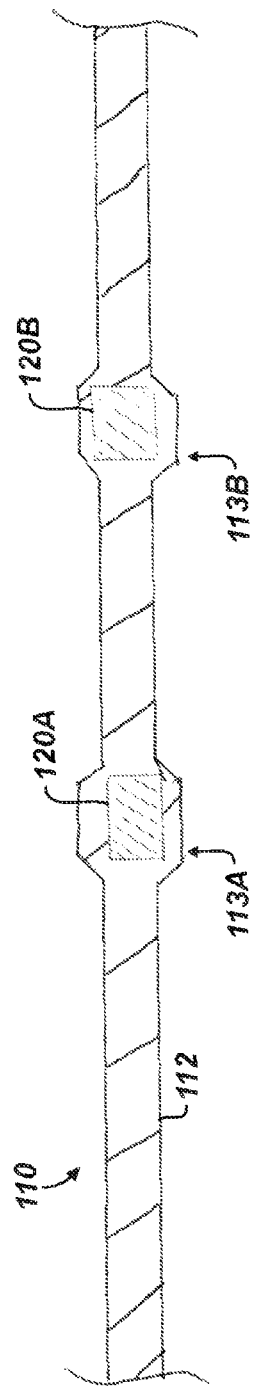

SEGMENTALLY RIGID SUTURE AND SUTURING TECHNIQUE

CROSS-REFERENCE TO RELATED APPLICATIONS

This application claims the benefit of U.S. Provisional Appl. No. 61/640,997, filed 1 May 2012, which is incorporated herein by reference.

BACKGROUND OF THE DISCLOSURE

Tearing or avulsion of soft tissue from bone is a relatively common type of injury, especially in sports, and can occur in many types of orthopedic injuries, such as torn or ruptured tendons and/or ligaments. In the shoulder, for example, portions of the rotator cuff tendons can tear within themselves or avulse from their insertion into the bone. FIGS. 1A-1B show superior views of a shoulder having a typically torn rotator cuff. Here, the tear is associated with the supraspinatus tendon as it inserts into the humerus. The subscapularis tendon and the coracoid process are also shown in FIG. 1A for reference.

The tear 10 shown in FIG. 1A is categorized as a simple tear because the tear branches normal to the muscle fibers, while the tear in FIG. 1B branches in both parallel and normal directions to the muscle fibers. In the case of both of these tears, such a torn rotator cuff can lead to pain, weakness, and loss of function.

In many cases, the rotator cuff is repaired by surgically reconnecting the edges of the torn muscle or tendon. Repairs may also include reconnecting the edges of any interstitial tear in the tendons, as well as approximating or reattaching the torn edge of the soft tissue to the bone where it originated. Common techniques for repairing tears to soft tissue and the avulsion of soft tissue from bone include using sutures through bone tunnels, suture anchors, friction anchors, tacks, screws with spiked washers and staples, or any combination of these techniques.

Any repair of a rotator cuff injury should have a secure fixation to soft tissue and should preserve the range of motion through which a muscle is expected to function after the repair. The fixation should also serve to provide a means for the soft tissue to anatomically reattach to a position in the shoulder, the humeral head in this case. In the shoulder, the soft tissues may experience wide ranges of motion, as shown by the views in FIGS. 2A-2B of a shoulder during internal and external rotations. In addition to these rotations, the shoulder may also be moved through adduction and abduction motions not shown. The various motions indicate that the soft tissue may undergo dramatic variations in stresses and that a wide variation in possible stresses at a particular point can occur. A surgical repair of injured soft tissue, such as the tears shown in FIGS. 1A-1B, preferably accounts for different requirements at various points along the injured site in order to alleviate concerns associated with the repair.

Failure of the repair is often instigated on the soft tissue site where, typically, suture is passed through the tendon in a number of ways. Failure occurs when the suture slices through the tendon while under tension. Common methods to alleviate this problem use multiple suture passes into the tendon using simple or mattress stitches. An alternative method uses complex stitches such as the massive cuff stitch.

FIG. 3A shows an example of the massive cuff stitch. A mattress stitch 131 is made horizontally in the tendon 20 and the suture tails are tied together, and a simple suture 130 is passed vertically medial to the mattress stitch 131 and is extended to a bone fixation point (not shown) by the suture tails 132. However, as seen in FIG. 3B, as the simple suture tails 136 receive a high enough load upon muscle contraction, the pass of the simple suture 130 tends to cut through the tendon 20 until it engages the tensile load of the mattress suture 133 at point 135. The distance that the suture 130 cuts though the tendon 20 can form a gap at the bone/tendon interface, which can inhibit the tendon 20 from healing to the bone.

The disclosed methods and products detailed below serve in part to address this and other issues.

SUMMARY OF THE DISCLOSURE

The suture device of the present disclosure incorporates rigid segments or components into or over suture, enabling the device to resist tensile and compressive loads and to protect soft tissue from suture pull-through. The suture device generally comprises of two components, a rigid segment as well as a standard high tensile strength suture to create a segmentally rigid suture device. The rigid segment may be comprised of any of a number of materials that are appropriate for use in the human body and provide the desired strength and stiffness for a particular application. The suture as well can comprise any known suture composition. Although the segmentally rigid suture device could be used with any prior art suture configuration for a soft tissue repair such as affixing tendon or ligament to bone, several suture stitch configurations are described, including a grip stitch, a knot-tying grip stitch, a straight-line grip stitch, and a reverse straight-line grip stitch. The experimental tensile testing results for a grip stitch with a segmentally rigid suture, a massive cuff stitch, and a grip stitch with traditional high tensile strength suture is shown. The grip stitch with a segmentally rigid suture yielded the highest ultimate failure load, least tissue cut through, and the most optimal mode of failure.

In one implementation, a suture device for repairing soft tissue has suture composed of a suture material and has at least one segment composed of a second material. The at least one segment is disposed on (e.g., positioned on, fit on, crimped on, embedded into, integrated in, etc.) the suture. Additionally, the at least one segment is longitudinally rigid, meaning that the at least one segment resists changes in its length from compressive or tensile loads—with compressive rigidity being of particular interest, as disclosed below. In general, the second material of the at least one segment can be the same as or different from the suture material.

The suture device affixes soft tissue with a stitch having at least one suture pass into the soft tissue, and the at least one segment disposes adjacent an outside surface of the soft tissue in the stitch adjacent the at least one suture pass. So situated, the at least one segment supports the suture device against the outside surface of the soft tissue and limits a compressive load on the soft tissue by the suture at the at least one suture pass. In this way, the segment resists the pull-through of the suture in the soft tissue.

Rather than just one pass, the stitch can have at least two passes into the soft tissue. In this instance, the at least one segment can be disposed adjacent the outside surface of the soft tissue in the stitch adjacent the at least two suture passes. Then, the at least one segment supports the suture device against the outside surface of the soft tissue and limits the compressive load by the suture on the soft tissue between the at least two suture passes.

The segment can be composed of various types of material, including, but not limited to, metal, titanium, plastic, polyethylene, thermoplastic, an orthopedic plastic, polyoxymethylene, polyetheretherketone, bioabsorbable material, biologic material, allograft bone, ceramic, or a combination thereof. In one implementation, the at least one segment can include first and second segments disposed at different points on the suture and separated by a length of the suture between them.

The at least one segment can define an internal passage through which at least a portion of the suture passes. For example, the at least one segment can define a cylindrical shaped body with a throughbore that positions on the suture. A retention feature may be disposed on a length of the suture and can limit the position of the at least one segment on the length of the suture. For example, the retention feature can be one or more knots formed with the suture that retains the at least one segment in place.

In other configurations, the at least one segment can define a passage therein that crimps onto at least a portion of the suture, the at least one segment can be integrally connected to the suture, or the at least one segment can be embedded in the suture. For example, the at least one segment can have first and second ends integrally connected to portions of the suture. In another example, at least a portion of the first material of the suture at least partially surrounds the at least one segment.

As hinted to previously, the at least one segment on the device limits a first portion of the suture at a first end of the at least one segment from moving toward a second portion of the suture at a second end of the at least one segment. Thus, when the at least one segment disposes adjacent soft tissue and a first portion of the suture passes into the soft tissue at a suture point, the at least one segment can limit tearing of the soft tissue by the first portion of the suture at the suture point because the segment limits the compressive load the suture puts on the soft tissue. Also, the at least one segment can limit tearing of the soft tissue by a portion of the suture when the suture is disposed against an outside of the segment.

The device as described above can be used with a number of stitches to repair soft tissue. In a first repair, a person using the suture device forms a loop with the suture device by passing opposing ends of the suture through soft tissue at first suture points. The ends of the suture device are then passed through the soft tissue at an intermediate suture point, and the ends of the suture device are then passed through the formed loop. At this point the ends can be pulled taught and affixed to another part of a person's body or to another structural component, such as a bone, fixture, or the like.

The suture device in this stitch limits a compressive load of the suture on the soft tissue between at least one of the first suture points and the intermediate point by positioning the at least one segment disposed on the suture device against an outside surface of at least one side of the soft tissue between the suture points. In some embodiments, the suture device can have at least two rigid segments or elements. Thus, a first portion of the suture device on one side of the soft tissue can be supported with one rigid segment on the suture device against the soft tissue between the first and intermediate suture points. Likewise, a second portion of the suture device on the one side of the soft tissue can be supported with the same or different rigid segment on the suture device against the soft tissue between the second and intermediate suture points. In this way, the suture device in the stitch limits the compressive load on the soft tissue by the suture between both of the first suture points and the intermediate suture point by positioning the one or more segments against the outside surface of the one side of the soft tissue between the suture points.

Additional rigid segments can be used. For example, a third portion of the suture device on an opposing side of the soft tissue can be supported with another rigid segment on the suture device against the soft tissue between the first and intermediate suture points. Likewise, a fourth portion of the suture device on the one side of the soft tissue can be supported with the same or different rigid segment on the suture device against the soft tissue between the second and intermediate suture points.

In a second repair, a person using the suture device forms a loop with a suture device by passing the suture device through soft tissue at first and second suture points. One of the ends of the suture is then passed through the soft tissue at an intermediate suture point and is passed through the formed loop. Passing the suture through the soft tissue can use only one suture end. For example, an anchor can be placed in the bone, and the anchor can have two ends of the suture coming out of it. Only one end of the suture can then be used to stitch through the soft tissue at the suture points. In any event, the two ends can then be pulled taught and knotted once the stitch is complete. A first portion of the suture device can be supported with a first rigid segment on the suture device against the soft tissue between the first and intermediate suture points. Likewise, a second portion of the suture device can be supported with a second rigid segment on the suture device against the soft tissue between the second and intermediate suture points.

In a third repair, a person using the suture device forms a loop with a suture device by passing first and second ends of the suture device through soft tissue at one or more first suture points. The first and second ends of the suture device are then passed through the soft tissue at a second suture point and are passed through the formed loop. A portion of the suture device on one side of the soft tissue is then supported with at least one rigid segment on the suture device against the soft tissue between the first and second suture points. In an additional configuration, another portion of the suture device on an opposite side of the soft tissue can be supported with at least one rigid segment against the soft tissue between the first and second suture points.

In a fourth repair, a person using the suture device passes the first and second ends of a suture device through the soft tissue at first and second suture points. A portion of the suture device on one side of the soft tissue is supported with at least one rigid segment on the suture device against the soft tissue between the first and second suture points.

In a fifth repair, a person using the suture device forms a loop with the suture by passing ends of the suture through soft tissue at a first suture point. The ends of the suture are then passed through the formed loop outside the soft tissue (i.e., beyond the end of the tendon or ligament). A portion of the suture device on at least one side of the soft tissue is then supported with at least one rigid segment on the suture device against the soft tissue between the first and second suture points.

In a sixth repair, a person using the suture device makes a simple stitch in soft tissue at one suture point. Then, using a separate suture, a mattress stitch is passed through the soft tissue at second and third suture points, and a knot is tied over the suture tail from the simple stitch. A portion of the suture device on one side of the soft tissue can then be supported with at least one rigid segment on the suture device against the soft tissue between the first suture point and the mattress stitch. Additionally, an additional rigid segment may be placed on the opposite side of the soft tissue on the mattress stitch between the second and third suture points.

In an seventh repair, a person using the suture device forms a loop with a suture device by passing opposing ends of the suture device through soft tissue at first point. After passing the opposing ends through a second suture point, the ends of the suture device are passed through the formed loop. A first portion of the suture device on one side of the soft tissue can then be supported with at least one rigid segment on the suture device against the soft tissue between the first suture point and the loop outside the soft tissue. Likewise, a second portion of the suture device on the one side of the soft tissue can be supported with at least one rigid segment on the suture device against the soft tissue between the second suture point and the loop.

The foregoing summary is not intended to summarize each potential embodiment or every aspect of the present disclosure.

BRIEF DESCRIPTION OF THE DRAWINGS

The following drawings form part of the present specification and are included to further demonstrate certain aspects of the present disclosure. The subject matter of the present disclosure may be better understood by reference to one or more of these drawings in combination with the detailed description of specific embodiments presented herein.

It is to be noted, however, that the appended drawings illustrate only exemplary embodiments of the present disclosure and are therefore not to be considered limiting of its scope for the inventive teachings which may admit to other equally effective embodiments. In addition, although the figures may depict embodiments wherein the components represent different devices or locations, they can be combined into a single device or location. In addition, a single component may be comprised of a combination of components.

FIG. 4A is an isometric view of a segmentally rigid suture device having one or more rigid components or tubes disposed on suture.

FIG. 4B is a cross-sectional view of the device in FIG. 4A.

FIG. 8 shows a portion of a suture device according to the present disclosure in which segments of suture are used in conjunction with a rigid component.

FIG. 9A is a cross-sectional view of another segmentally rigid suture device having rigid sections and flexible sections integrally connected together.

FIG. 9B is a cross-sectional view of a segmentally rigid suture device having rigid components incorporated or embedded inside flexible suture.

DETAILED DESCRIPTION OF THE DISCLOSURE

Figure 1A:
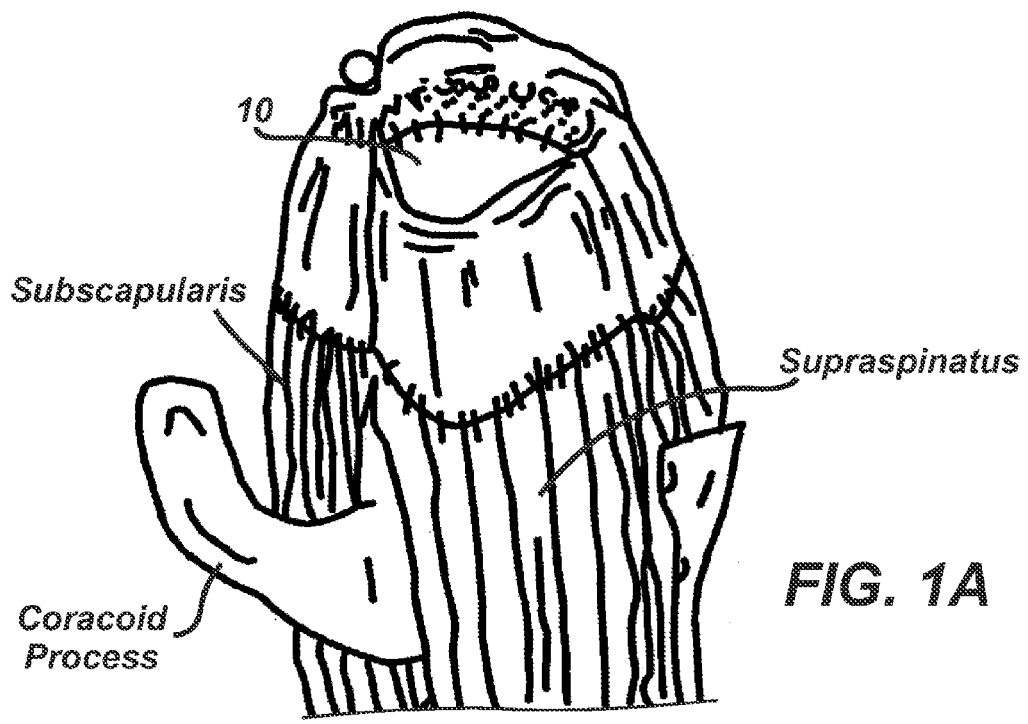
FIG. 1A is a superior view of the shoulder and rotator cuff demonstrating a tear in the rotator cuff
Figure 1B:
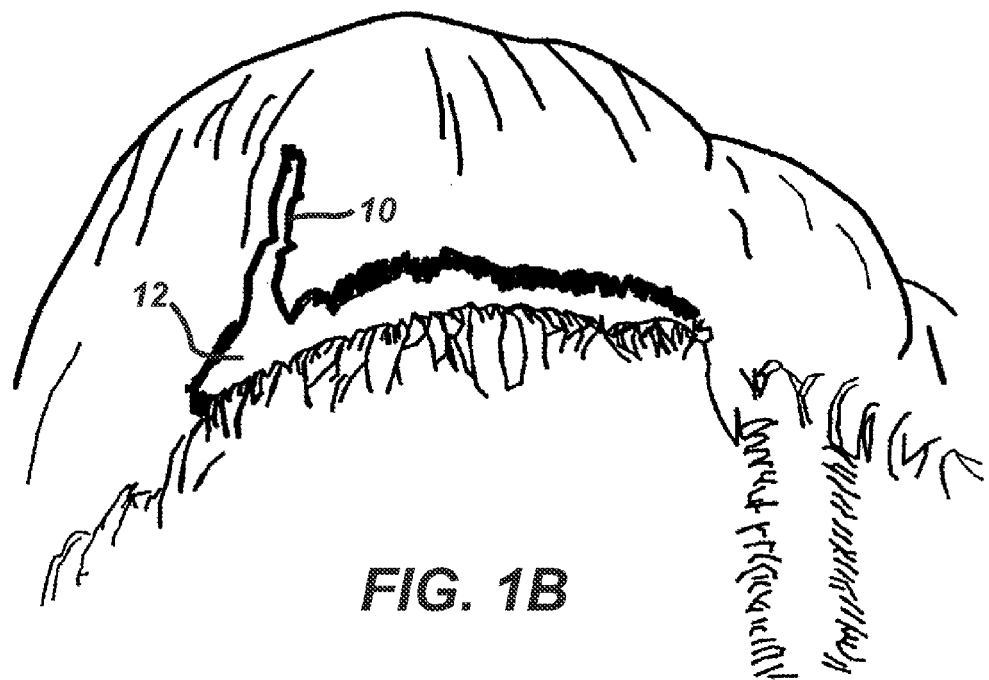
FIG. 1B is a superior view of the shoulder and rotator cuff demonstrating a tear in the rotator cuff.
Figure 2A:
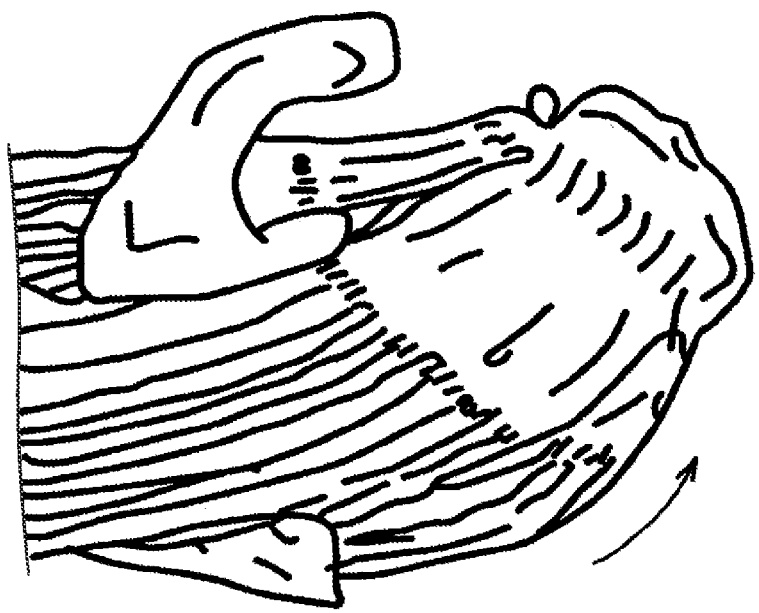
FIGS. 2A-2B are superior views of the shoulder and rotator cuff in full internal rotation and full external rotation, respectively.
Figure 2B:
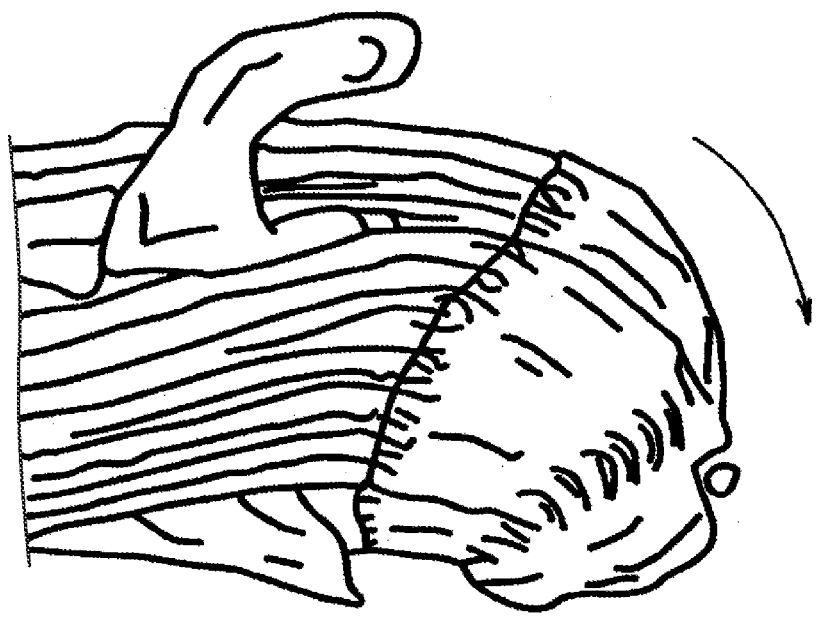
Figure 3A:
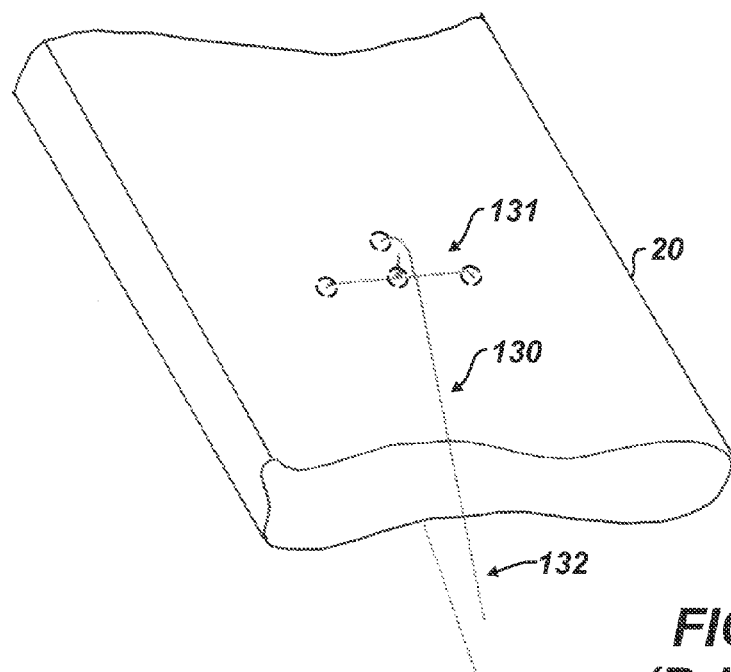
FIG. 3A is a view of a massive cuff stitch with a simple pass and mattress stitch according to the prior art.
Figure 3B:
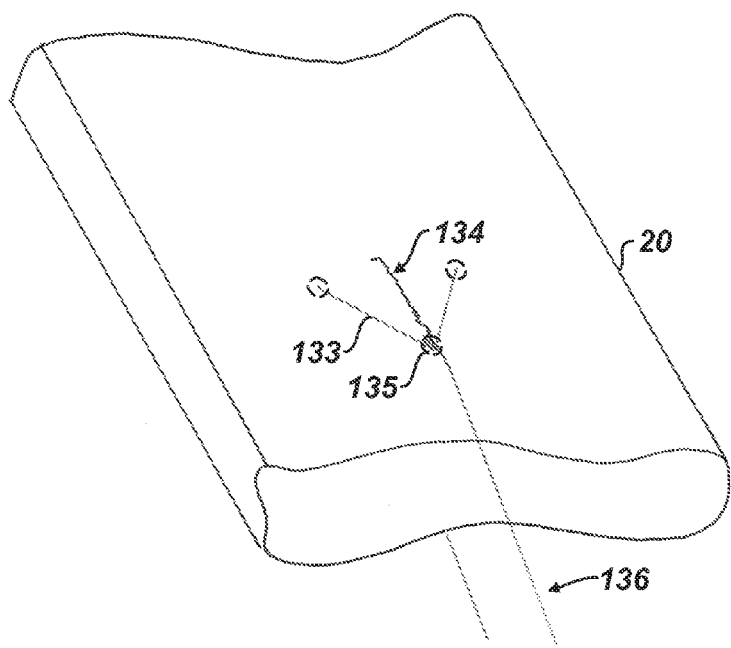
FIG. 3B is a view of the massive cuff stitch in which the simple stitch has pulled partially through the tendon.

The subject matter of the present disclosure overcomes the shortcomings of current soft tissue repair techniques by disposing rigid components on suture, enabling the device to resist both tensile and compressive loads. For illustrative purposes, embodiments of the present disclosure and associated methods are described for use to repair rotator cuff tears. The techniques shown are compatible with arthroscopic surgery, however, it should be noted that those skilled in the art will recognize that the teachings of the present disclosure could use non-arthroscopic techniques to repair the soft tissue injuries without departing from the spirit or scope of the present invention. Those skilled in the art will recognize that the present disclosure can be used to repair other soft tissue injuries without departing from the spirit or scope of the present invention.

Before turning to the particular stitches disclosed herein for use in repairing soft tissue injuries, discussion first turns to a number of segmentally rigid suture devices 110 for use with the particular stitches, which are described later.

A. Segmentally Rigid Suture Devices

Referring first to FIGS. 4A-4B, a segmentally rigid suture device 110 according to the present invention includes rigid segment or component 113A-B disposed on a high tensile strength suture 112. The rigid component 113A-B is rigid longitudinally along its length, meaning that the component 113 resists changes in its length from compressive or tensile loads—with compressive rigidity being of particular interest, as disclosed below. In general, the length of rigid components 113A-B is selected for the application in order to accommodate the size of a surgical stitch. The strength, stiffness, profile, and surface durometer/softness of the rigid components 113A-B are each selected so that compression loads are resisted while damage to the soft tissue is avoided. Additionally, the rigid components 113A-B may be comprised of any of a number of materials that are appropriate for use in the human body and provide the desired strength and stiffness for a particular application. Examples of materials that may be used to construct the rigid component include, but are not limited to, metal (e.g., titanium), plastic (e.g., polyethylene), an orthopedic plastic (e.g., polyoxymethylene such as manufactured under the trade name DELRIN), organic polymer thermoplastic (e.g., polyether ether ketone (PEEK)), bioabsorbable materials, biologic materials, and/or combinations of these materials.

As shown, the rigid segments or components 113A-B can be independent, external elements 114, shown here having a cylindrical shape, although any suitable shape could be used. These external elements 114 preferably have an inner diameter near the outer diameter of the high tensile strength suture 112, as seen in FIG. 4B. Ideally, the external elements 114 have a minimal wall thickness to reduce the volume of the suture device 110 when in place in a human body. The edges of the external elements 114 are preferably smooth enough not to cut through the suture 112 but are preferably able to resist the forces placed on them during contraction of the rotator cuff as discussed below.

In this implementation, the rigid components 113A-B using the external elements 114 are allowed to slide up and down the suture 112 for ease of implementation. Although the device 110 in FIGS. 4A-4B is shown having only two rigid components 113A-B, any number of rigid components 113A-B may be added to the suture 112 to create a segmentally rigid suture device 110. Additionally, the rigid components 113A-B may be provided preassembled on the suture 112 or may be assembled by a user on the suture 112 during surgery.

Figure 5A:
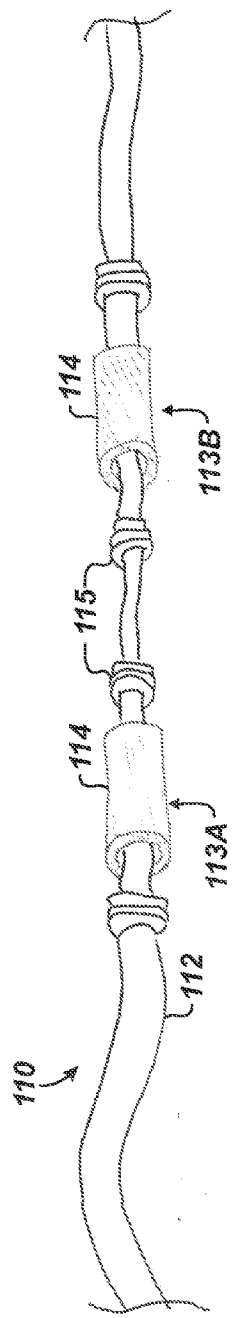
FIG. 5A is an isometric view of another segmentally rigid suture device where one or more rigid components or tubes are disposed on suture and prevented from sliding past a particular point by a series of knots.

Referring to FIG. 5A, an alternative configuration of a segmentally rigid suture device 110 is shown having rigid segments or components 113A-B on suture 112 as discussed above with reference to FIGS. 4A-4B. Again, the rigid components 113A-B use external elements 114, such as the cylindrical elements discussed above. However, knots or any other such suture based surface 115 are disposed on the high tensile strength suture 112. The knots 115 may allow for some or no sliding of the external elements 114 over the suture 112. Any combination of sliding, limited sliding, and non-sliding of the external elements 114 may be used to create the segmentally rigid suture device 110.

Rather than knots 115, the external elements 114 can be affixed in place on the suture 112 using adhesive, shrink fitting, heat treatment, welding, etc. Moreover, the external elements 114 can engage the suture 112 to limit sliding or make sliding difficult for the external elements 114 relative to the suture 112 by interfacing the surface of the suture 112 and the surface of the external component 114 as discussed below with reference to FIGS. 6A, 6B, 7A, and 7B.

Figure 6A:
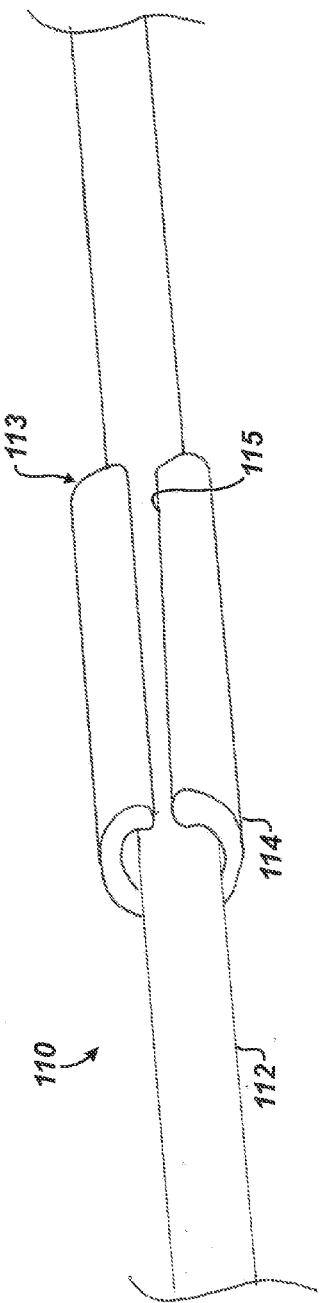
FIGS. 6A and 6B show a rigid component for a segmentally rigid suture device in which the rigid component can slide along suture (FIG. 6A) and can then be deformed to grip the suture and be held permanently in place (FIG. 6B).
Figure 6B:
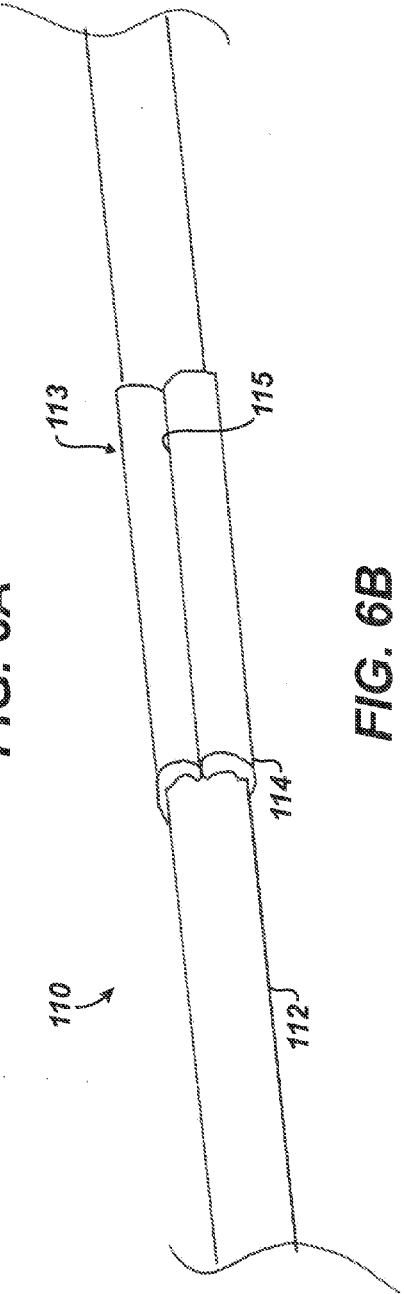

In one arrangement, for example, a rigid segment or component 113 for a segmentally rigid suture device 110 can be able to slide along the length of the suture 112 as shown in FIG. 6A. The ability to slide the rigid component 113 allows a surgeon to manipulate the placement of the rigid component 113 when making a stitch to best suit the needs of the stitch and the location of the component 113 in the stitch. At some point in making the stitch, the surgeon can then deform or crimp the rigid component 113 to grip the suture 112 so the rigid component 113 is held permanently in place, as shown in FIG. 6B. As shown, the rigid component 113 can be an external element 114, such as a sleeve, having a split 115 along its length that allows the element 114 to be closed around the suture 112 when crimped.

Figure 7A:
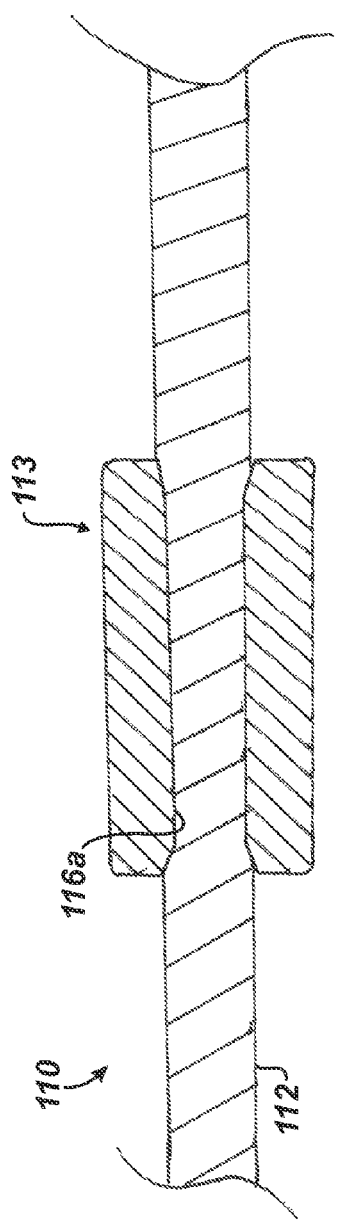
FIG. 7A shows a rigid component for a segmentally rigid suture device in which the rigid component has an internal surface or retention features that increase the difficulty of the rigid component to slide along suture in both directions.
Figure 7B:
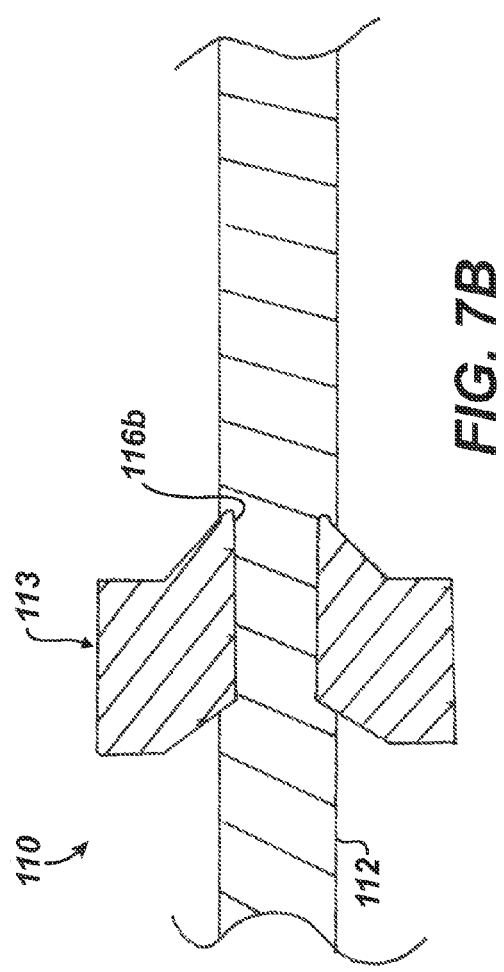
FIG. 7B shows a rigid component for a segmentally rigid suture device in which the rigid component has an internal surface or retention features that limit sliding along suture in one direction.

Other than knots, adhesive, crimping, etc., a rigid segment or component 113 as shown in FIG. 7A for a segmentally rigid suture device 110 can have an internal surface or features 116a that limit sliding along the suture 112 in both directions. The internal surface or features 116a can use teeth, grooves, forks, threading, interference fits, or the like, which engages the suture 112 and prevents or makes difficult the sliding of the component 113. Alternatively, a rigid component 113 as shown in FIG. 7B for a segmentally rigid suture device 110 can have an internal surface or feature 116b that limits sliding along the suture 112 in only one direction. This may allow the surgeon to manipulate the placement of the rigid component 113 in a stitch, but may prevent slippage of the component 113 from that placement, which may be beneficial in some stitching techniques.

Referring to FIG. 8, a portion of a suture device 110 according to the present disclosure is shown. As understood herein, the suture 112 of the suture device 110 of the present disclosure can include a continuous length of suture or may comprise several segments of suture connected or associated together to make the desired length of suture. With this understanding, the device 110 in FIG. 8 has segments 112a-b of suture used in conjunction with a rigid component 113. One segment 112a of suture 112 passes through the rigid component 113 and affixes with a retention feature, such as a knot 115a, beyond one end of the component 113. Likewise, another segment 112b of suture 112 passes through the rigid component 113 and affixes with a retention feature, such as a knot 115b, beyond the other end of the component 113.

A similar configuration of using suture segments 112a-b in conjunction with a rigid component 113 can apply to any of the other types of suture devices 110, sutures 112, and rigid components 113 disclosed herein, such as in FIGS. 6A-6B and 7A-7B as well as FIGS. 9A-9B and 10A-10E disclosed below. As will be appreciated, should one of the suture segments (e.g., 112a) break, the rigid component 113 can still be held by the other segment 112b and may not come loose in a person's body. As with this and other devices 110 disclosed herein, the suture 112 with its segments 112a-b and the rigid component 113 can be pre-assembled before surgery or can be assembled during surgery as the case may be. If assembled during surgery, for example, the surgeon may tie a knot 115a on an end of a suture segment 112a and then pass suture segments through a rigid component 113. Then, the surgeon may repeat this with the other segment 112b.

Referring to FIG. 9A, another configuration of a segmentally rigid suture device 110 is shown in a cross-sectional view, again having rigid segments or components 113A-B on suture 112. Here, the rigid components 113A-B use integral elements or sections 118A-B disposed between high tensile strength sections 116A-C of the suture 112. The integral sections 118A-B are made rigid to the point of resisting loads typically experienced by a soft tissue repair for which the device 110 is used. The integral sections 118A-B can be produced through the use of heat treatment of the suture 112, material changes made to the suture 112, application of adhesives or other material infused in the suture 112, a change in the threading pattern of the high tensile strength suture 112, making a series of knots or structural features with suture 112, or the like. Any number of integral sections 118A-B may be used along the length of the suture device 110. The length of the integral sections 118A-B may also be of any length to optimize the necessary compressive/tensile properties of the suture device 110 across a specific suture stitch configuration.

Referring to FIG. 9B, yet another configuration of a segmentally rigid suture device 110 is shown in a cross-sectional view, again having rigid segments or components 113A-B on suture 112. For this device, the rigid components 113A-B have rigid, embedded elements 120A-B encapsulated by the high tensile strength suture 112 at multiple sections. Any number of rigid embedded elements 120A-B may be used along the length of the suture 112. The length of the rigid embedded elements 120A-B may also be of any length to optimize the necessary compressive/tensile properties of the suture across as specific suture stitch configuration.

As before, the embedded elements 120A-B may be comprised of any of a number of materials that are appropriate for use in the human body and provide the desired strength and stiffness for a particular application. Examples of materials that may be used to construct the embedded elements 120A-B include, but are not limited to, titanium, polyethylene, an orthopedic plastic (e.g., manufactured under the trade name DELRIN), PEEK, bioabsorbable materials, biologic materials, and/or combinations of these materials.

The high tensile strength suture 112 captures the embedded elements 120A-B so that there may be no ability for the embedded elements 120A-B to slide along the suture 112. The suture 112 surrounding the embedded elements 120A-B is preferably strong enough to hold the embedded elements 120A-B in place but also selected so that the diameter of the rigid components 113A-B does not impair the repair of the soft tissue.

As will be appreciated, forming a rigid element 118 for the device 110 in FIG. 9A or embedding a rigid element 120A for the device 110 in FIG. 9B depends on the style and material of the suture 112 used. As will also be appreciated, the surgical suture 112 can come in different types, sizes, materials, and the like. In general, the suture 112 is a thread composed of biological or synthetic materials, which may or may not be absorbable in the human body. Example materials include chromic catgut, nylon, polydioxanone (PDS), polyglycolic acid (Dexon), prolene, polyactic acid, caprolactone, polypropylene, polyester, polyethylene, silk, stainless steel wire, and the like. Diameters of the suture 112 can range from 0.01-mm to 1.0-mm, for example.

The suture 112 may also be braided or non-braided. A braided or multifilament suture has several thin strands or filaments of the suture material twisted together. A non-braided suture is a single strand or monofilament of the suture material or a suture composed of woven suture material. Given this understanding of sutures, one skilled in the art will recognize that a number of manufacturing techniques can be used to construct a suture device 100 as disclosed herein having a suture 112 with an integrated or embedded element 118/120A. One particular implementation of an embedded element is described below.

Figure 10A:
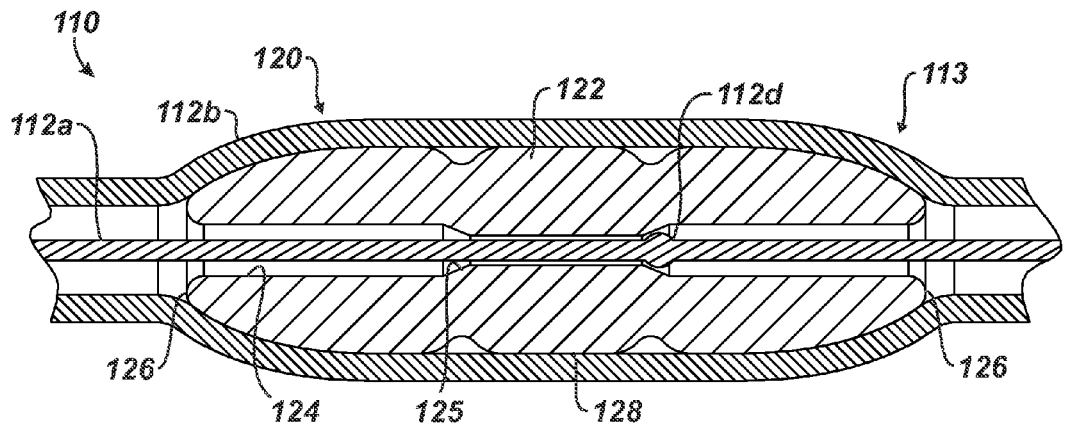
FIG. 10A is a cross-sectional view of one embodiment of a segmentally rigid suture device having a rigid segment or component incorporated or embedded in flexible suture.
Figure 10B:
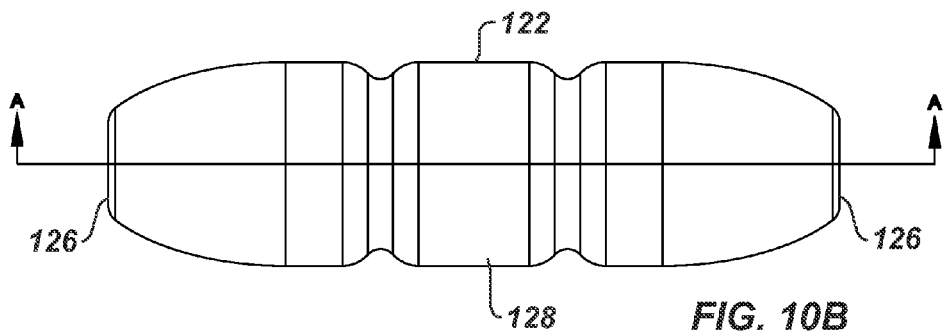
FIG. 10B is a side view of the rigid component for the suture device of FIG. 10A.
Figure 10C:
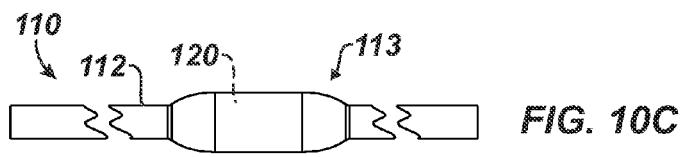
FIG. 10C shows a side view of the suture device in FIG. 10A having one rigid component.
Figure 10D:
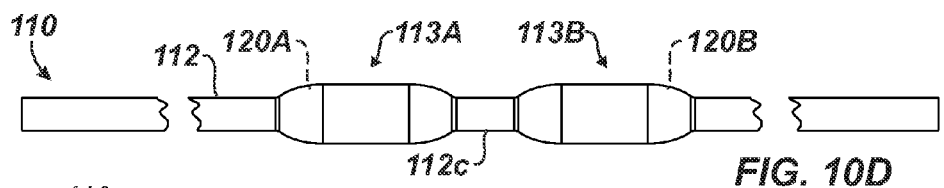
FIG. 10D shows a side view of the suture device in FIG. 10A having two rigid components separated by a length of suture.

Referring to FIG. 10A, details of a particular implementation of an embedded configuration for the segmentally rigid suture device 110 of FIG. 9B is shown in a cross-sectional view. As before, the device 110 has a rigid segment or component 113 embedded in suture 112. Again, the rigid component 113 is a rigid, embedded element 120 encapsulated by the high tensile strength suture 112. Any number of rigid embedded elements 120 may be used along the length of the suture 112. For example, FIG. 10C shows one embedded element 120, while FIG. 10D shows two embedded elements 120A-B separated by a central section 112c of suture 112.

As before, the embedded element(s) 120 may comprise any of a number of materials that are appropriate for use in the human body and that provide the desired strength and stiffness for a particular application. Examples of materials that may be used to construct the embedded element(s) 120 include, but are not limited to, titanium, polyethylene, an orthopedic plastic (e.g., manufactured under the trade name DELRIN), PEEK, bioabsorbable materials, biologic materials, allograft bone, ceramic, and/or combinations of these materials. The length of the rigid embedded element(s) 120 may also be of any length to optimize the necessary compressive/tensile properties of the suture 112 across a specific suture stitch configuration. In one example, the length of the element 120 for a #2 suture size can be about 6-mm.

As shown in FIG. 10A, the high tensile strength suture 112 preferably captures the embedded element 120 so that the embedded element 120 cannot slide along the suture 112. Thus, the suture 112 surrounding the embedded element 120 is preferably strong enough to hold the embedded element 120 in place but also selected so that the diameter of the rigid component 113 does not impair the repair of the soft tissue.

In the embodiment of FIG. 10A, the suture 112 includes a core 112a and a sheath 112b. The sheath 112b can be stronger than the core 112a and can constitute high tensile strength suture. Alternatively, the core 112a can be the stronger portion of the suture 112, and the sheath 112b can be a less robust outer braiding. Thus, the core 112a can constitute high tensile strength suture, rather than having the sheath 112b constitute high tensile strength suture. Still further, both the core 112a and the sheath 112b can be high tensile strength suture material.

In the particular implementation shown, the embedded element 120 is a cylindrical body or tube 122 defining an internal bore 124 therethrough. The bore 124 can define an internal restriction 125, and the ends 126 of the body 122 can be contoured. Additionally, the external surface 128 of the body 122 may define various gripping features, such as grooves or the like. These aspects of the embedded element 120 can facilitate manufacture and use of the device 110, as detailed below.

As is known, sutures can be formed using braiding machines that have a number of movable carriers with bobbins. The bobbins hold filaments of the suture material, and a core feeding system is situated below a housing for the carriers. The filaments are taken off of the carriers and form an apex of a braid at a distance above the bobbins. Above the braid's apex is a collection wheel that pulls the formed suture upward and at a uniform tension.

For assembly, the rigid body 122 of the element 120 installs on the core 112a of suture material with the core 112a disposed through the internal bore 124 of the body 120. The suture core 112a can be a mono-filament of suture material, can be several filaments run or braided together, or can be a high tensile strength suture. To help hold the body 122 in place on the core 112a, a knot, bulge, crimp, adhesive, or other retaining feature 112d can be used between the core 112a and the body's bore 124. As shown, the feature 112a can be a knot in the core 112a that engages in or against the bore 124 and/or restriction 125 of the body 122.

Externally, the suture sheath 112b may be at least partially formed or passed over the core 112a and the rigid body 122 to encapsulate the body 122 as the embedded element 120. The suture sheath 112b can comprise braided or woven filaments formed around the outside surface of the body 122. To do this during manufacture, the body 122 can be held onto the core 112a via crimping, adhesives, knot, or other such feature 112d, and the core 112a can feed into the braiding of the sheath 112b in a manner similar to how cores are fed in braided suture using take-up to control the feed rate.

Any external features, such as grooves or the like, on the external surface 128 of the body 122 can further help maintain the element 120 in place in the sheath 112b. During braiding, such features on the external surface 128 may also help the filaments to flow into a braid around the body 120. Still, the core 112a in the suture 112 may be beneficial in keeping the rigid element 120 from slipping through the braided sheath 112b during use in surgery.

Figure 10E:
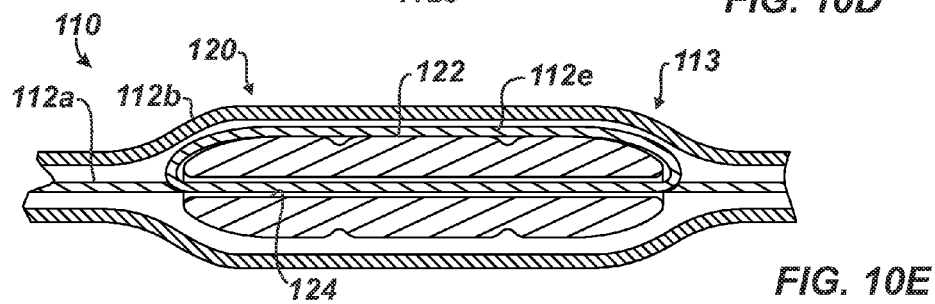
FIG. 10E shows a cross-sectional view of another embodiment of the segmentally rigid suture device similar to FIG. 10A.

As an alternative to the use of the retention feature 112d and restriction 125 as shown in FIG. 10A, other forms of retention can be used. As shown in FIG. 10E, for example, the embedded element 120 is a cylindrical body or tube 122 defining an internal bore 124 therethrough. A core 112a of the suture 112 passes through the body's bore 124, and a sheath 112b of the suture 112 passes over the body 122. A wrapping, loop, or tie 112e formed in the core 112a around the body 122 helps hold the body 122 in place. As can be seen, the wrapped embodiment represents an alternative way to retain the body 122.

B. Stitches Using Segmentally Rigid Suture Devices

With an understanding of the segmentally rigid suture device 110 for use in repairing soft tissue injuries, discussion now turns to FIGS. 11A-11F and 12A-12C to illustrate two types of stitches, referred to herein as a grip stitch and a knot-tying grip stitch, for repairing a soft tissue injury. In one difference between the grip stitch and knot-tying grip stitch, suture tails for the grip stitch are disposed on the same side of the tendon, whereas the suture tails for the knot-tying grip stitch are disposed on opposite sides of the tendon. Additionally, the knot-tying grip stitch has its suture pass through a bone/screw interface and a knot is tied across the suture tails so that the suture for this stitch is typically, but not necessarily, preassembled into a suture anchor or other bone/suture interfacing device. These and other details are discussed below.

Figure 11A:
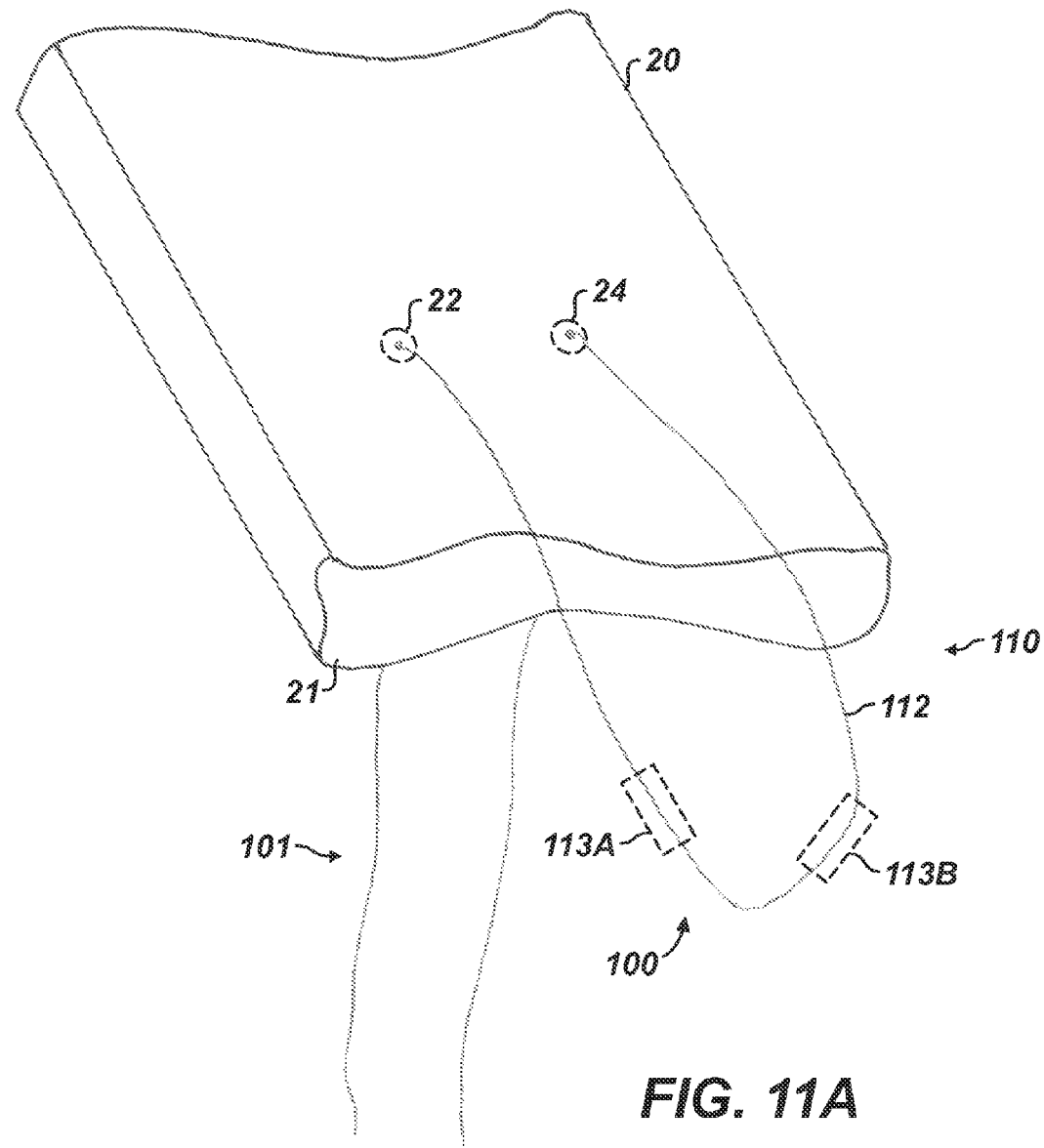
FIGS. 11A-11D shows steps for performing a grip stitch in a rotator cuff tendon using a segmentally rigid suture device of the present disclosure.

FIG. 11A shows a first step of creating a grip stitch, which can be performed arthroscopically if desired. As one option, the grip stitch can use only suture 112 without rigid components. As will be addressed in detail below, the grip stitch based on suture alone can offer advantages over prior art techniques.

As an alternative, the grip stitch can use any one of the segmentally rigid suture devices 110 discussed above. For illustrative purposes, rigid segments or components 113A-B of the segmentally rigid suture devices 110 of FIGS. 4A-4B are shown in dashed representation on the suture 112. As will be appreciated, any one of the suture device 110 disclosed here can be used and can use any of the various forms of rigid components 113. As discussed above, for example, two such rigid components 113A-B can be external elements (114: FIG. 4A) disposed on the suture 112, external elements (114: FIG. 5A, 6A, etc.) held in place on the suture 112, integral sections (118A-B: FIG. 9A) of the suture 112, or embedded elements (120A-B: FIG. 9B) encapsulated in the suture 112. In preferred arrangements, the segmentally rigid suture device 110 of FIG. 5A (or even FIGS. 6A through 7B) is used because the external rigid components 113 incorporated onto the suture 112 and held in place by knots 115 or other features on the suture 112 (or by the elements 114 holding onto the suture 112 or by separate suture segments 112a-b held to the component 113) reduce the chances of a rigid component 113 becoming loose in the human body should the suture 112 break. The same reasoning applies to the use of rigid components 113 as in FIGS. 9A-9B.

To begin the grip stitch, a surgeon uses the tails 101 of the device 110 to begin a mattress stitch in the tendon 20. Each tail 101 is passed through adjacent suture points 22 and 24 in the tendon 20 near to the tendon's torn edge 21 requiring fixation to bone (not shown). This is only diagrammatically depicted in the figures. Before completing the mattress stitch, the loop 100 of the mattress stitch is not pulled tight against the tendon 20. Instead, the loop 100 is maintained. For example, the surgeon may hold the mattress stitch's loop 100 extracorporeally (not shown).

As shown, the suture device 110 has rigid components 113A-B disposed toward the midpoint of the suture 112 about where the looped end 100 is to be formed. These components 113A-B can be preassembled (i.e., fixed in place) on the suture device 110. Alternatively, they may be slid in place on the device 110 during the stitching and may later be crimped or affixed to the suture 112, depending on the embodiment used. These and other possibilities will be appreciated by one skilled in the art. Thus, operators can position a rigid component 113 on the suture device 110 against the outside surface of the soft tissue by adding the component 113 as an independent element in place on the suture 112 of the suture device 110 during the operation or by having the component 113 already added to (i.e., already positioned in place on, fit on, crimped on, embedded in, integrated into, etc. as disclosed herein) the suture 112.

Figure 11B:
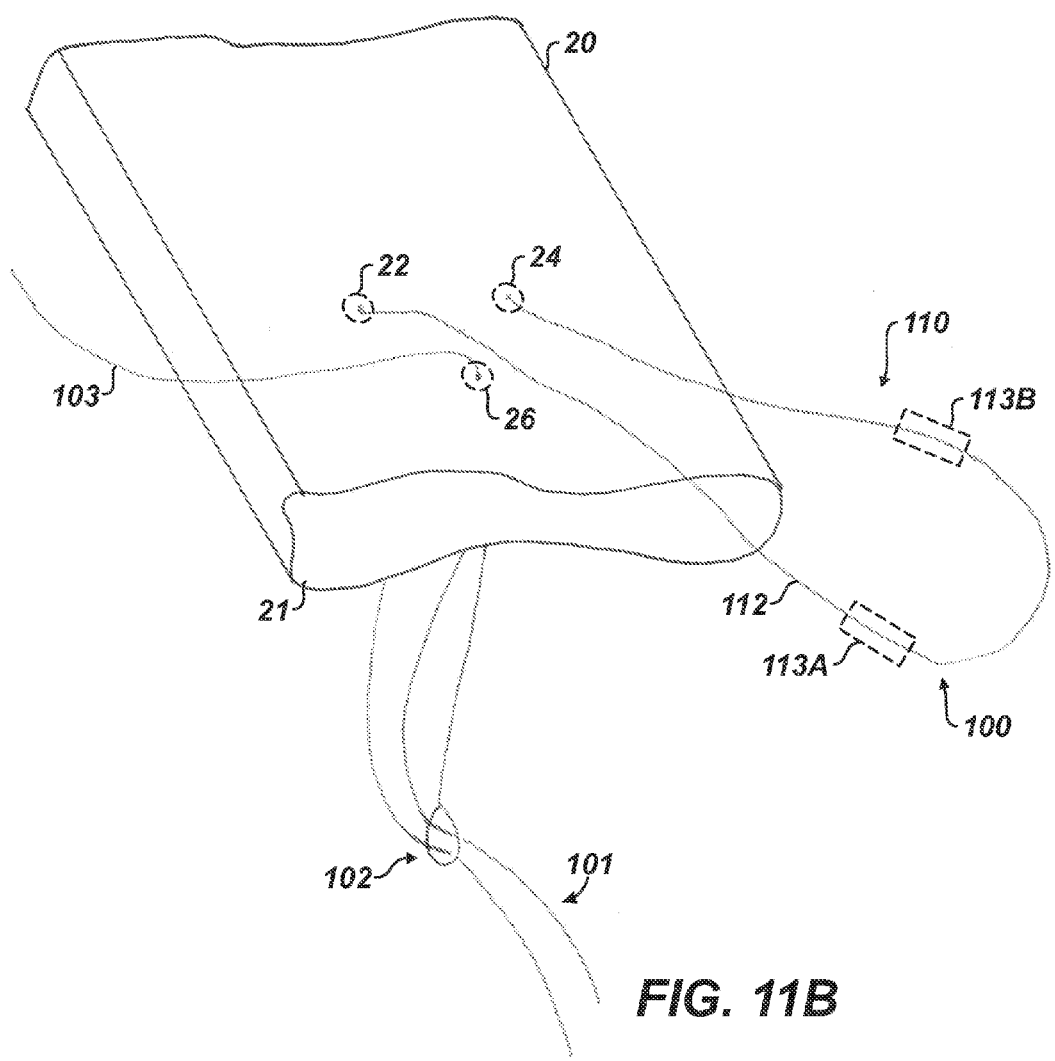
Figure 11C:
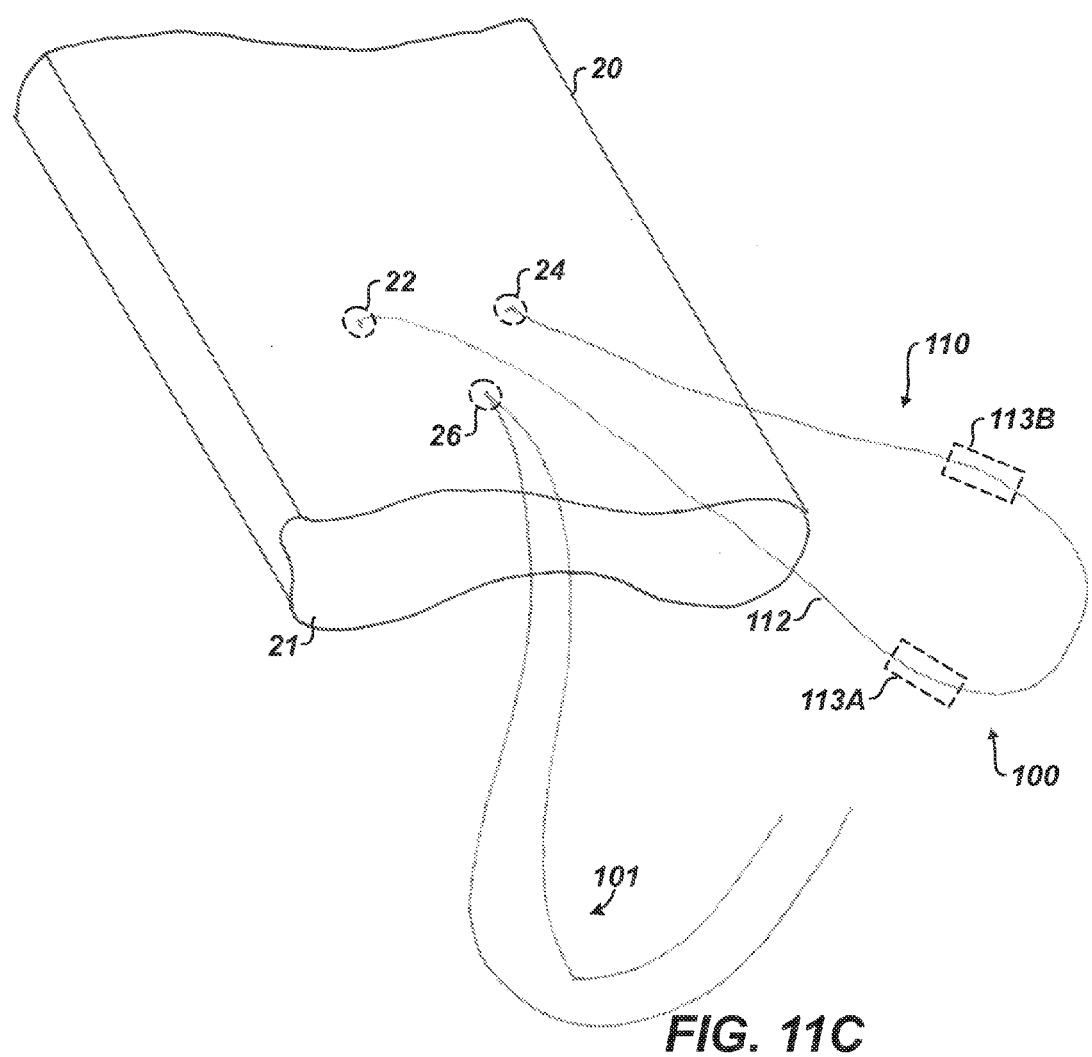

FIG. 11B shows the next step to create the grip stitch. The surgeon passes the tails 101 of the suture device 110 through a suture shuttling device, such as the one shown as 102, although other devices could be used. The surgeon then passes the shuttle's tail 103 through the tendon 20 laterally to the mattress stitch. This produces a triangular pattern of suture points 22, 24, and 26. The surgeon then retrieves the suture shuttling device 102 which passes the suture tails 101 through the same central point 26 in the tendon 20 as seen in FIG. 11C. Conceivably, it is possible that the ends of the suture 112 can be passed independently through roughly the same intermediate point 26 or can be passes independently through at least two associated intermediate points 26. This applies to this and other suture points or passes of the suture through the soft tissue disclosed herein.

Figure 11D:
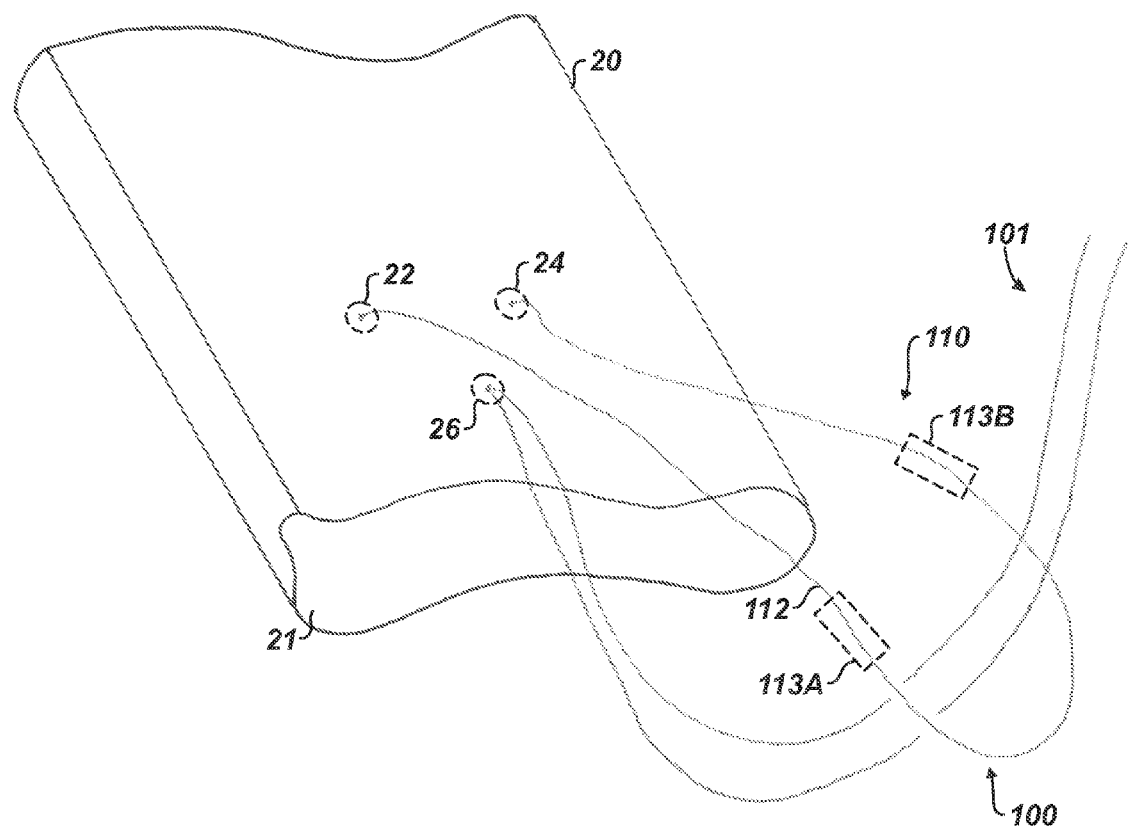

The next step to create the grip stitch is shown in FIG. 11D. Here, the surgeon passes the suture tails 101 through the loop 100 in the suture 112. At this point, the surgeon completes the grip stitch by affixing the tails 101 of the device 110 to bone using a bone tunnel, knotless anchor, or other fixation technique (not shown).

Figure 11E:
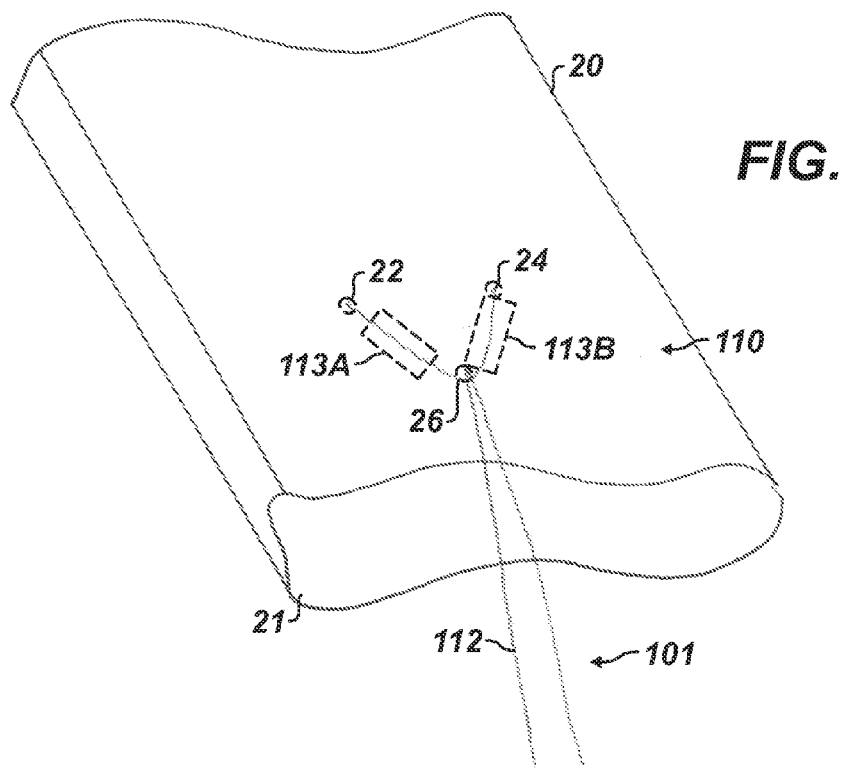
FIG. 11E shows one side of the rotator cuff tendon with the completed grip stitch.

FIG. 11E shows one side of the tendon 20 with the completed grip stitch. The suture tails 101 are incorporated into the bone side of the repair using a fixation (not shown). Because the suture loop 100 is engaged by the suture tails 101, a pre-tensioning effect is seen by the tendon 20 which is not seen in some other complex stitch configurations of the prior art, including the massive cuff stitch. The rigid components 113A-B of the device 110 are shown disposed between the central stitch point 26 and the splayed points 22 and 24.

Figure 11F:
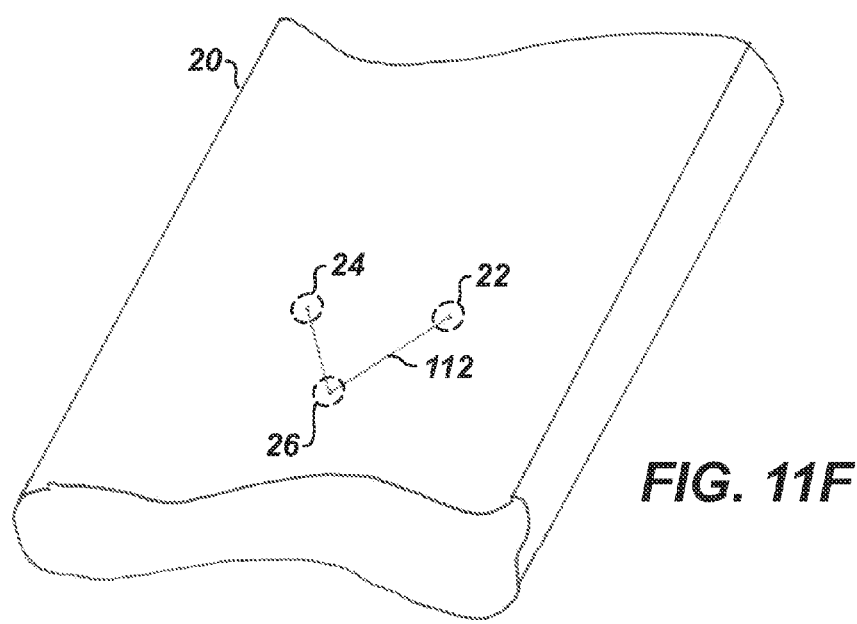
FIG. 11F shows the opposite side of the rotator cuff tendon with the completed grip stitch.

FIG. 11F shows the other side of the tendon 20 opposite that seen in FIG. 11E. This side also shows the completed grip stitch. It is noted that both suture tails 101 extend from the same side of the tendon 20. As shown here in FIG. 11F, no rigid components are used between the central stitch point 26 and the splayed points 22 and 24 on this side of the tendon 20. However, in other configurations, rigid components (not shown) can be used here in a manner comparable to the other side of the tendon 20 shown in FIG. 11E.

At least two components 113A-B as shown are preferred. It will be appreciated that the benefits of the present disclosure can still be realized with only one such component 113A or 113B used or more components used on the other side (FIG. 11F). Either way, each component 113A and/or 113B supports the suture device 110 against the outside surface of the soft tissue 20 and limits the compressive load on the soft tissue between at least two suture passes by the suture through the soft tissue. As noted above, the component 113 is longitudinally rigid, meaning that the components resist changes in its length from compressive or tensile loads—with compressive rigidity being of particular interest. Thus, for example, the component 113A limits a first portion of the suture 112 for the first suture pass 24 at a first end of the component 113A from moving toward a second portion of the suture 112 for the other suture pass 26 at a second end of the component 113A. In this way, the component 113A limits the compressive load on the soft tissue that the portions of suture 112 would subject the soft tissue to if the compressive rigidity of the component 113A were not present. In essence, the portions of suture 112 when placed in tension would tend to want to come or squeeze together, which puts compressive loads on the soft tissue between the portions of the suture 112. The compressive rigidity of the component 113A runs counter to the compressive load that the portions of suture 112 attempts to place on the soft tissue between the suture points. The same applies to the other component 113B.

Figure 12A:
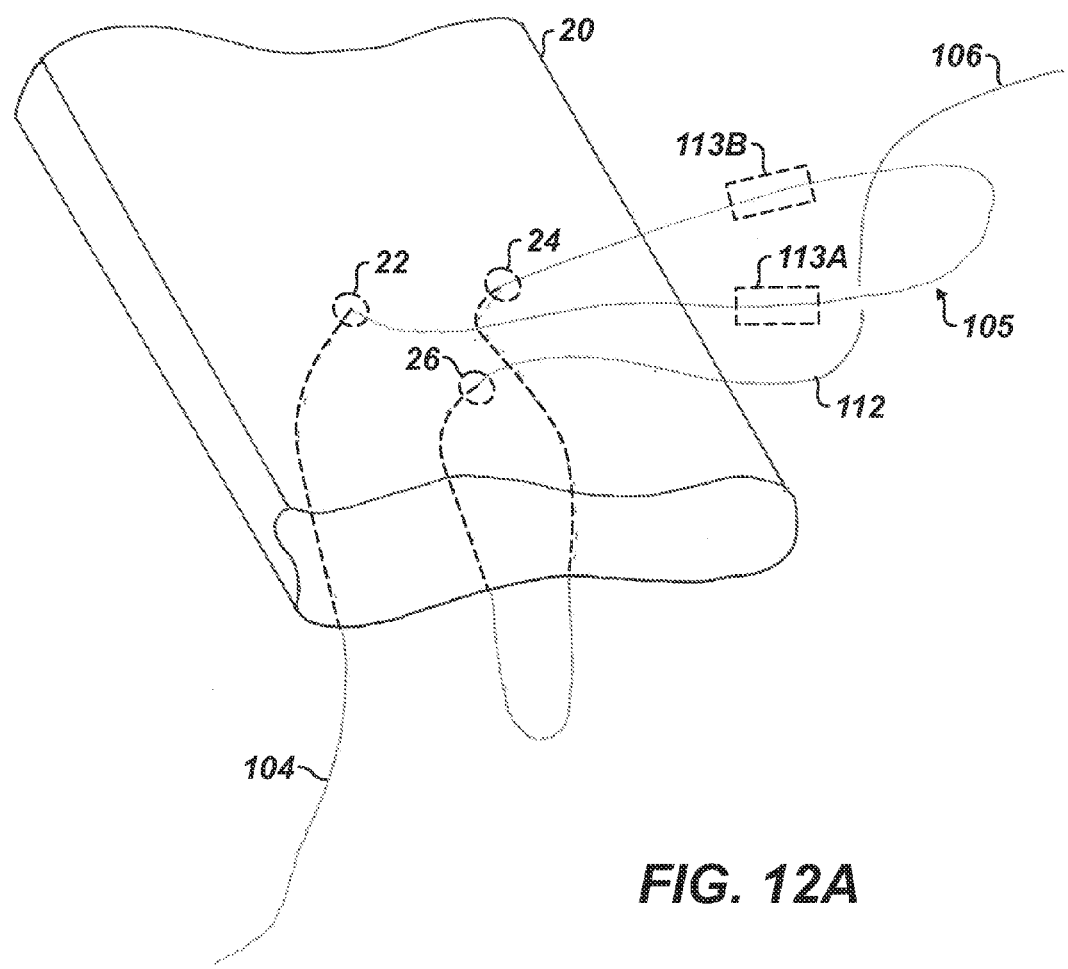
FIG. 12A shows a rotator cuff tendon with a segmentally rigid suture device in a stage of making a knot-tying grip stitch.
Figure 12B:
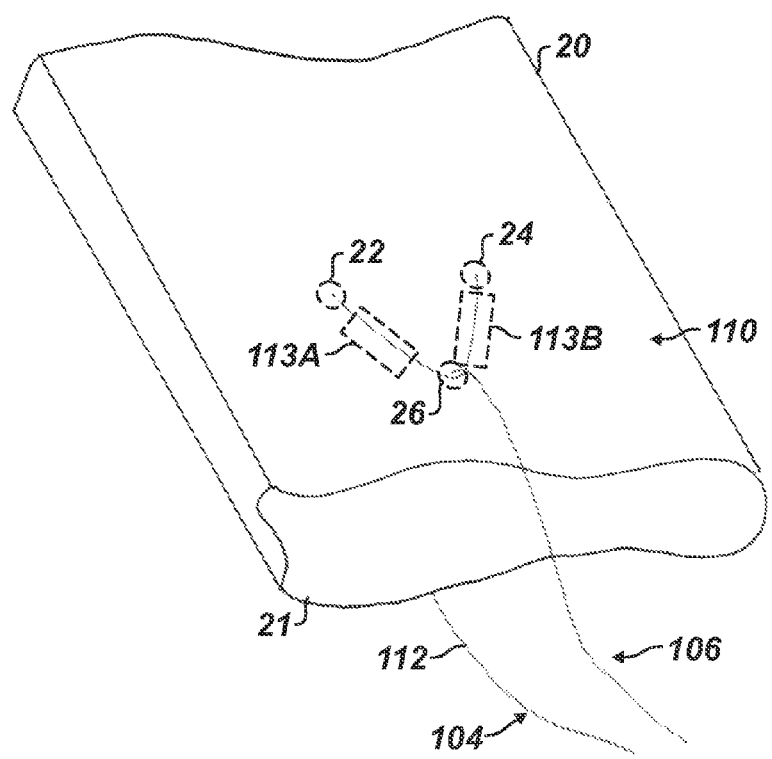
FIG. 12B shows one side of the rotator cuff tendon with a completed knot-tying grip stitch.
Figure 12C:
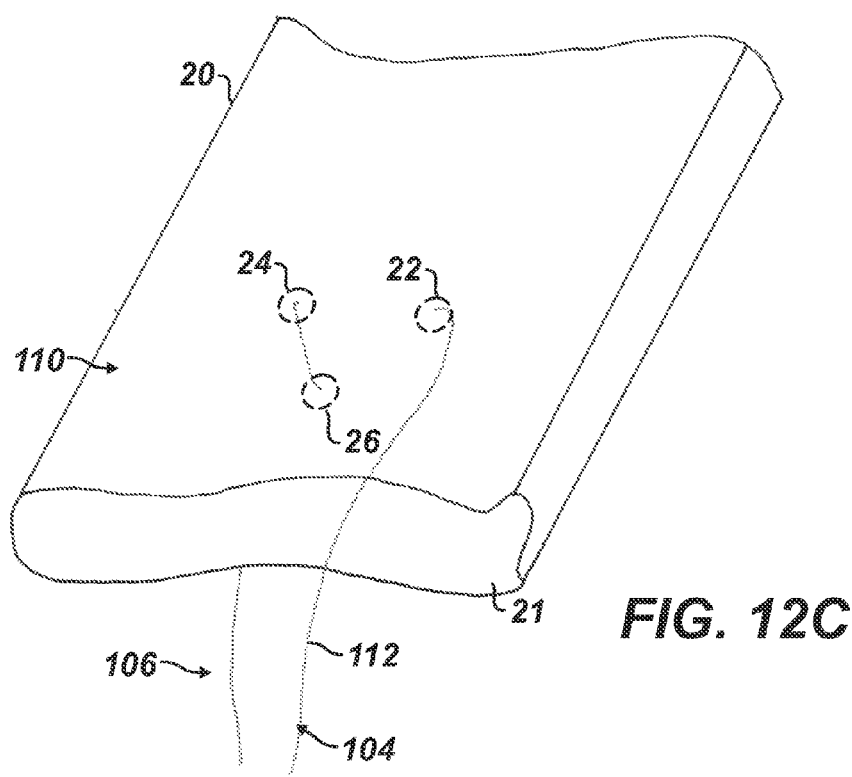
FIG. 12C shows the opposite side of the rotator cuff tendon in FIGS. 12A-12B with a completed knot-tying grip stitch.

FIGS. 12A-12C illustrate a knot-tying grip stitch for repairing a soft tissue injury using suture alone or using a segmentally rigid suture device 110. As shown in FIG. 12A, the surgeon passes enough of the suture 112 necessary to create the knot-tying grip stitch through suture points 22, 24, and 26 arranged in the triangular pattern in the tendon 20. For example, one suture tail 106 is passed through one of the splayed points 22 on the tendon 20 and passed through the other splayed point 24, creating a loop 105 on which the rigid components 113A-B are disposed. This suture tail 106 is then passed through the tendon 20 through the central point 26 and passed through the loop 105.

The other suture tail 104 may already come preassembled on a suture anchor or other bone fixation device, which fixes this tail 104 to bone. For example, the tail 104 may be located through the eyelet of a suture anchor, some facet of a bone fixation device, bone tunnel, or the like. It is seen that the suture loop 105 is similar to that used to create the grip stitch in that the free suture tail 106 is passed through the loop 105 to create a grasping-like stitch. To complete the repair, this free suture tail 106 is pulled snug and tied in a knot to the suture tail 104 already affixed to the bone fixture (not shown).

FIG. 12B shows one side of the tendon 20 with the knot tying grip stitch in the tendon 20. Because the suture loop 105 is engaged by the suture tail 106, a pre-tensioning effect is seen by the tendon 20 which is not seen in some other complex stitch configurations of the prior art, including the massive cuff stitch. As before, the rigid components 113A-B of the device 110 are shown disposed between the central stitch point 26 and the splayed points 22 and 24.

FIG. 12C shows the opposite side of the tendon 20 shown in FIGS. 12A-12B, revealing the other side of the completed knot tying grip stitch. It is noted that suture tail 104 extends from one side of the tendon 20, while the other suture tail 106 extends from the other side of the tendon 20. Although not shown, a rigid component may be used on the suture 112 between the suture points 24 and 26.

Figure 13A:
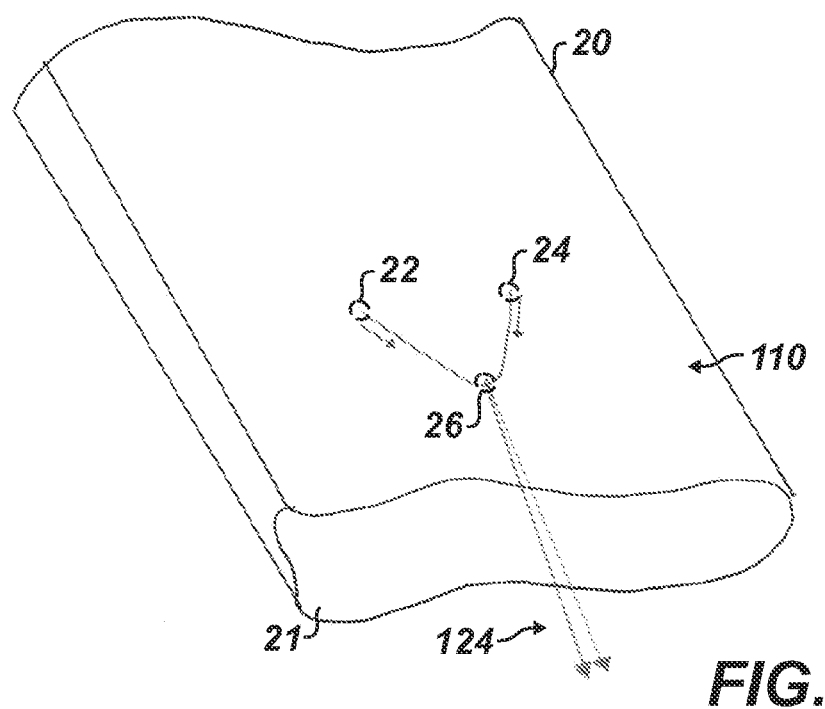
FIG. 13A is a view of a grip stitch using suture alone, in which the direction that the suture tends to pull through the tendon is indicated when tension is placed on the suture's tails.

As discussed above, the disclosed segmentally rigid suture device 110 (FIGS. 4A through 10D) can be used in a grip stitch (FIGS. 11A-11F) and a knot-tying grip stitch (FIGS. 12A-12C). Either of the stitches can use suture alone without the suture device 110 and may still provide a suitable stitch to affix the tendon to bone. For example, FIG. 13A shows a grip stitch when the suture tails 124 are placed in tension by muscle contraction. Stitch points 22 and 24 have a cinching effect similar to a lasso when stress is placed on the tendon 20.

Figure 13B:
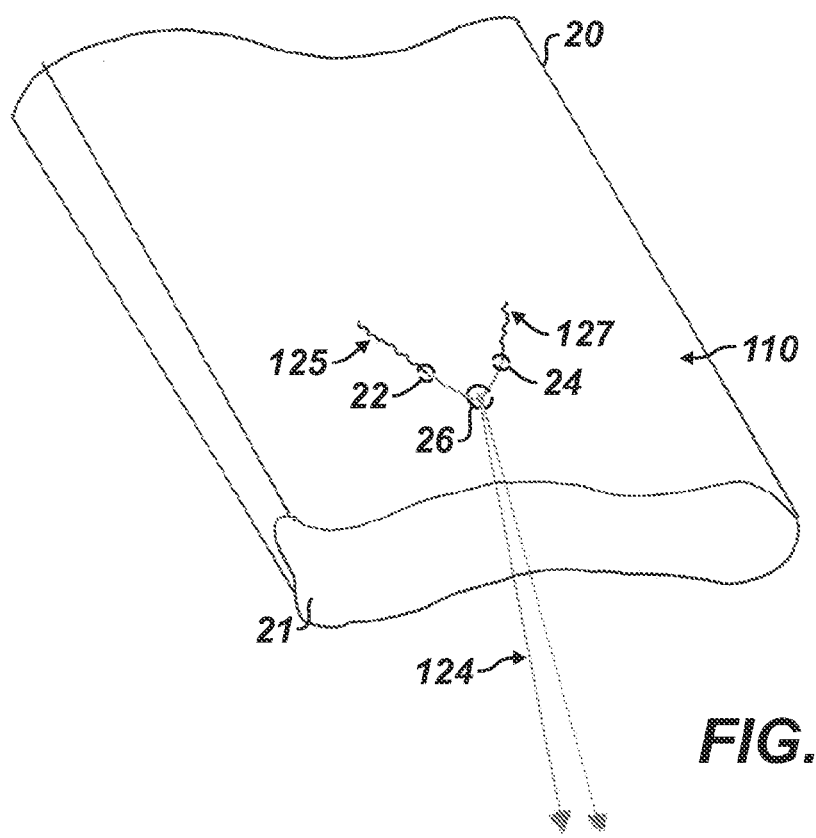
FIG. 13B is a view of a grip stitch using suture alone, in which the suture has pulled through the tendon as tension is placed on suture's tails.

As shown in FIG. 13B, the suture passes at points 22 and 24 may have a tendency to cut through the tendon 20 in the direction of the arrows shown in FIG. 13A. This tendency may be created for any stitch configuration which has a component in which the suture grabs onto itself, including but not limited to the grip stitch and the knot tying grip stitch. As shown in FIG. 13B, the stress on the tendon 20 from the muscle contraction may be greater than the strength of the tendon 20, and the stitches at points 22 and 24 may begin to cut through the tendon 20 as shown by 125 and 127. In other words, the compressive load on the tendon 20 by suture 112 between the suture points 22 and 26 and between the suture points 24 and 26 exceeds the strength of the tendon 20 as the suture at these various points 22, 24, and 26 attempt to come together. The distance that the suture cuts through the tendon 20 produces a gap at the bone/tendon repair site, which can inhibit the tendon 20 from healing to the bone (not shown). Therefore, it is preferred that tearing of the tendon 20 be minimized.

Accordingly, it may be preferred to use the segmentally rigid suture device 110 according to the present disclosure for the grip stitch, the knot-tying grip stitch, a straight-line grip stitch, a reverse straight-line grip stitch, and any other stitches disclosed herein. Nevertheless, it will be appreciated with the benefit of the present disclosure that the segmentally rigid suture device 110 can also be applied to any stitch, not just the grip stitch or knot-tying grip stitch. For example, the segmentally rigid suture device 110 can be used with and can enhance the strength of a massive cuff stitch, a vertical mattress stitch, a horizontal mattress stitch, a modified mason-allen stitch, a simple stitch, or any other stitch configuration known and used in the art. (Details related to using the suture device 110 with other stitches are provided below with reference to FIGS. 18A through 21B.) Either way, however, the grip stitch or the knot-tying grip stitch alone or either of these stitches using the disclosed suture device 110 can significantly reduce tearing of the tendon 20 when subjected to loads.

Incorporating the segmentally rigid suture device 110 into the stitch configuration can help to alleviate part or most of the suture cut-through shown in FIG. 13B. All previously described versions of a segmentally rigid suture device 110 are options of application in the following methods although only a few versions are shown in FIGS. 14A-14C.

Figure 14A:
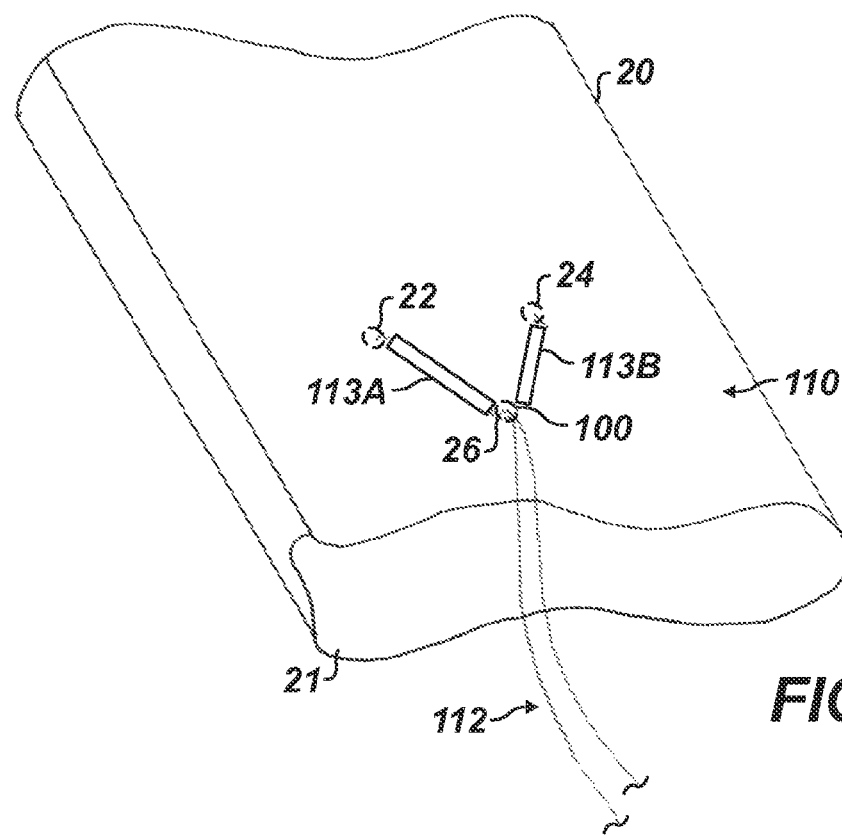
FIG. 14A shows a segmentally rigid suture device with the rigid components incorporated with or into the suture and implemented into a grip stitch on a rotator cuff tendon.

Turning to FIG. 14A, a grip stitch is shown in which two rigid components 113A-B are placed between the suture passes. The rigid components 113A-B act in compression when the suture tails 112 are loaded in tension. In this way, the rigid components 113A-B can potentially prevent some or all of the suture pull-through seen above. The central loop 100 of the suture 112 acts on itself in this configuration.

Figure 14B:
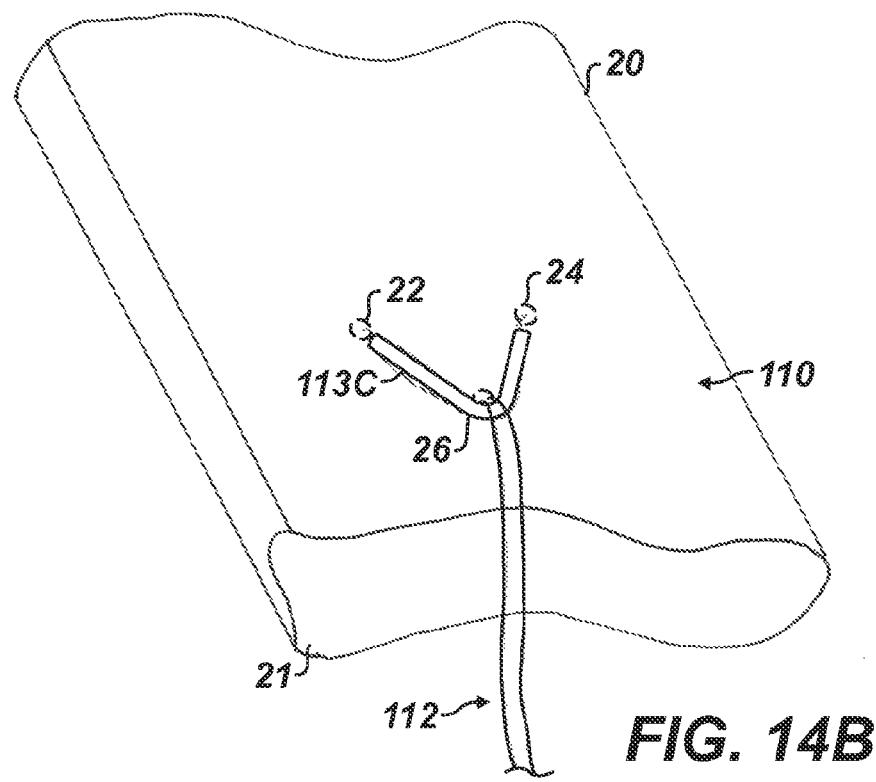
FIG. 14B shows a segmentally rigid suture device with one rigid component incorporated with or into the suture and implemented into the grip stitch on a rotator cuff tendon.
Figure 14C:
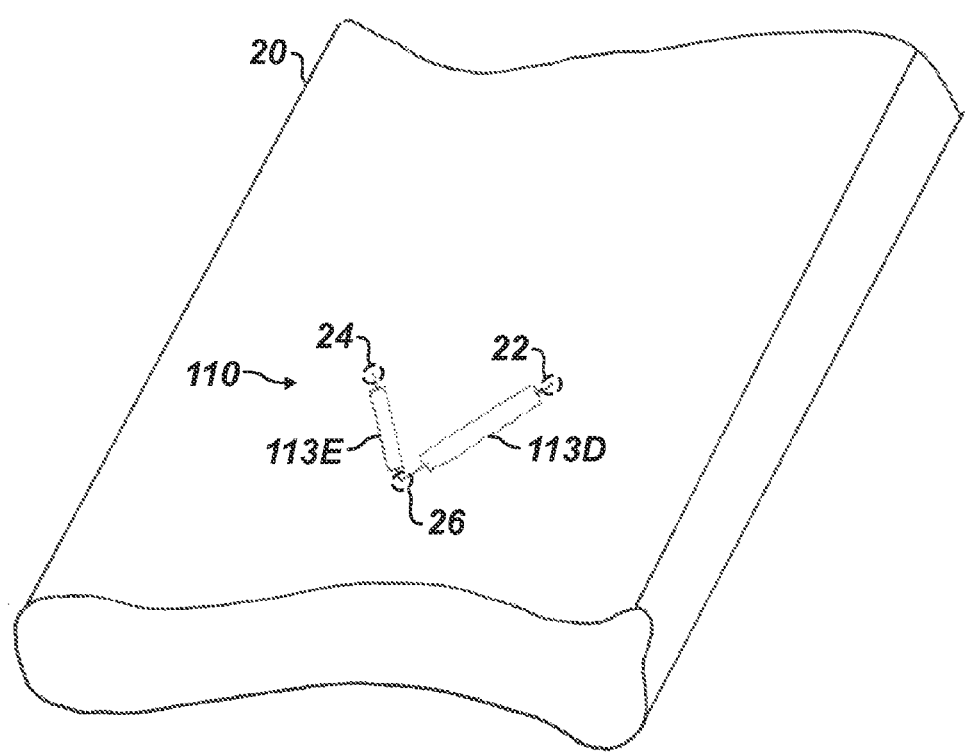
FIG. 14C shows the opposite side of the rotator cuff tendon in FIGS. 14A-14B with the segmentally rigid suture device having additional rigid components.

As an alternative to the two rigid components 113A-B, FIG. 14B shows a grip stitch in which one rigid component 113C of a suture device 110 spans the suture loop portion of the stitch. The suture tails 101 pull directly against this single rigid component 113C in this configuration. This single component 113C can be completely rigid or have segmental rigidity. Thus, the component 113C can be rigid and preconfigured with the angled shape. As a segmentally rigid element, however, the component 113C can be a rigid cylinder with a flexible central component, which allows the device 110 to be bent when the stitch is completed.

As noted above, the other side of the tendon 20 may not include rigid components. As also hinted to briefly above, the other side of the tendon 20 may actually include one or two rigid components. As shown in FIG. 14C, an example of two components 113D-E can be used on the opposite side of the tendon 20 illustrated in FIGS. 14A-14B. In each of the circumstances shown in FIGS. 14A-14C, the stress of the tendon 20 in compression is transferred to the rigid components of the suture device 110 and protects the tissue from suture cut-through.

In addition to the grip stitch and knot-tying grip stitch, other stitches can exhibit benefits over prior art stitches when suture is used alone or when a segmentally rigid suture device 110 is used in conjunction with the stitch. Additional stitches are disclosed in FIGS. 15A through 17B. These stitches are shown using a segmentally rigid suture device 110 with one or more rigid components 113 as disclosed herein. It will be appreciated, however, that these additional stitches could be performed with suture 112 only. In addition, it will be appreciated that any one of the suture device 110 disclosed here can be used and can use any of the various forms of rigid components 113.

Figure 15A:
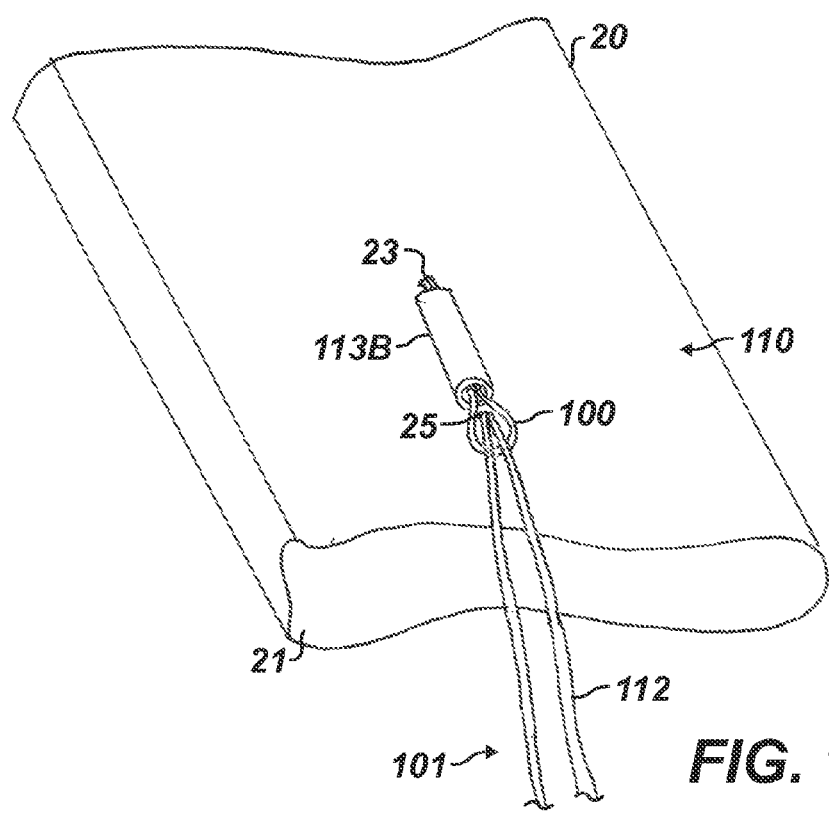
FIG. 15A shows a straight-line grip stitch according to the present disclosure using a segmentally rigid suture device.
Figure 15B:
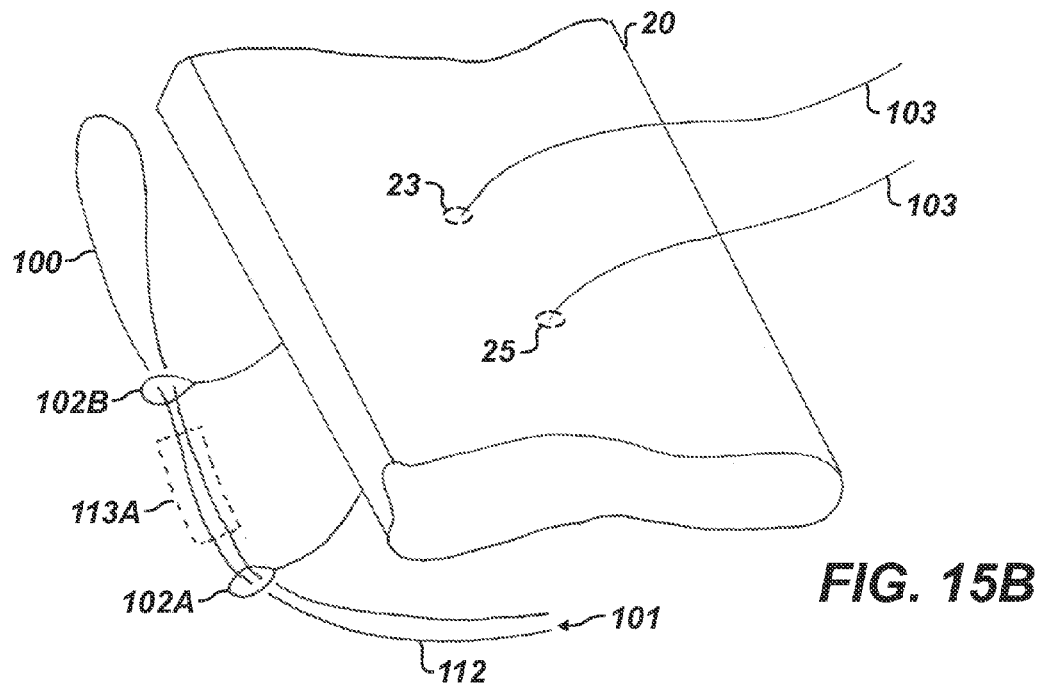
FIGS. 15B-15D shows steps for performing the straight-line grip stitch of FIG. 15A.

Turning to FIG. 15A, a straight-line grip stitch according to the present disclosure is shown using a segmentally rigid suture device 110. As shown in FIG. 15B, the suture device 110 has tail ends 101 and a looped end 100. A rigid component 113A can be used on the looped end 100 or the tail ends 101, but this is not strictly necessary because some arrangements of this stitch may not use this component 113A. Shuttles 102A-B are passed through in-line suture points 23 and 25 in the tendon 20. The surgeon passes the tail ends 111 through the front shuttle 102A and passes the looped end 100 through the back shuttle 102B.

Figure 15C:
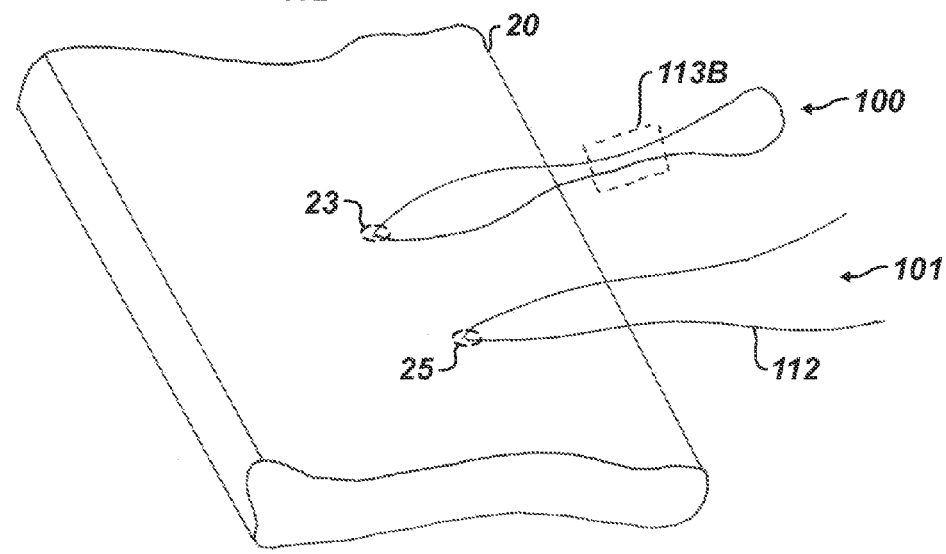
Figure 15D:
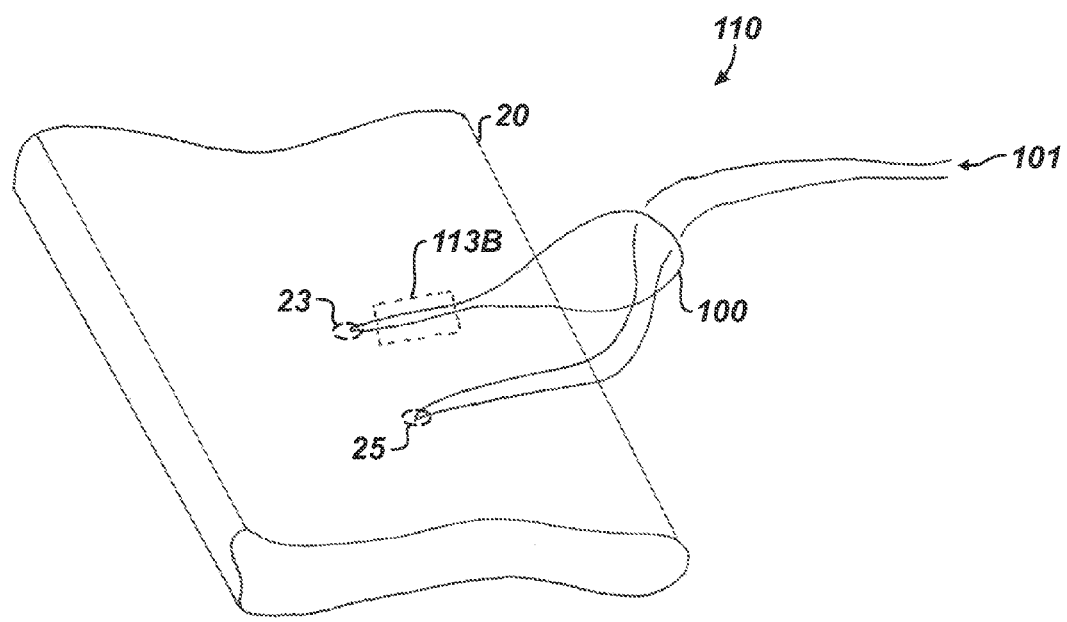

The tails 103 of the shuttles 102A-B are pulled through the tendon 20 to bring the looped end 100 and the tail ends 101 of the device 110 through the suture points 23 and 25 as shown in FIG. 15C. Another rigid component 113B may be positioned on the looped end 100 of the suture 112, and then the surgeon passes the tail ends 101 through the looped end 100 as shown in FIG. 15D. At this point, the stitch can be pulled tight, and the surgeon can affix the components 113A-B to the suture 112, if needed, by crimping or the like. Finally, the tail ends 101 of the device 100 affix to a bone fixation as discussed herein (i.e., FIGS. 23A-23B) to produce the straight-line grip stitch as shown completed in FIG. 15A. Although the crimping of the components 113A-B is described as being done during the stitching processes, it will be appreciated that the surgeon can complete the particular stitch (as well as others discussed herein) and can then crimp or otherwise affix the components 113A-B to the suture 112.

Figure 16A:
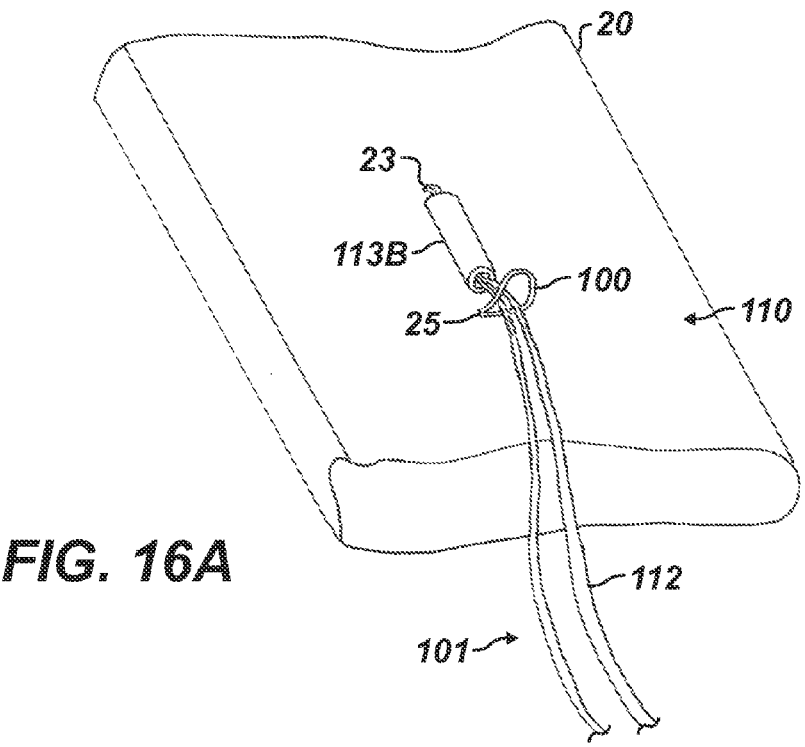
FIG. 16A shows a reverse straight-line grip stitch according to the present disclosure using a segmentally rigid suture device.
Figure 16B:
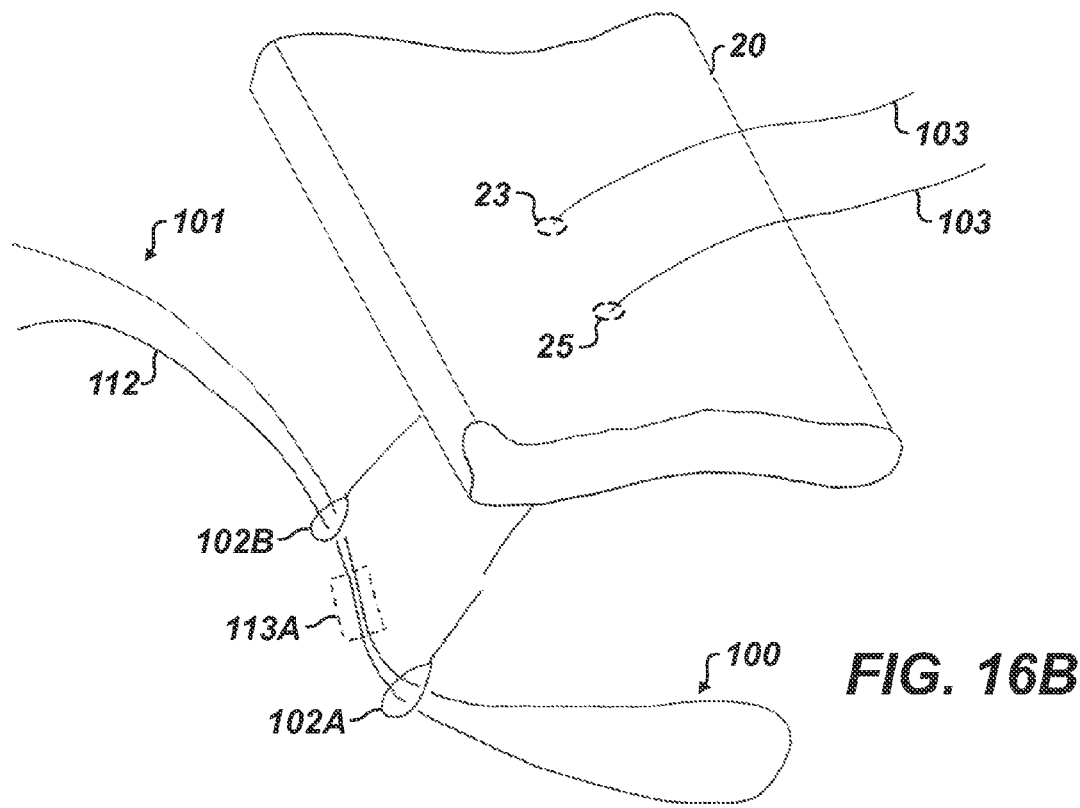
FIGS. 16B-16D shows steps for performing the reverse straight-line grip stitch of FIG. 16A.

Turning to FIG. 16A, a reverse straight-line grip stitch according to the present disclosure is shown using a segmentally rigid suture device 110. This reverse straight-line grip stitch is similar to the straight-line grip stitch of FIG. 15A, but has a reverse arrangement. As shown in FIG. 16B, the suture device 110 again has tail ends 101 and a looped end 100, and the looped end 100 or the tail ends 101 may pass through a rigid component 113A, although this is not strictly necessary. Likewise, the rigid component 113A may be already pre-assembled on the suture 112. In any case, shuttles 102A-B are passed through in-line suture points 23 and 25 in the tendon 20. Contrary to the previous stitch, the surgeon passes the tail ends 111 through the back shuttle 102B and passes the looped end 100 through the front shuttle 102A.

Figure 16C:
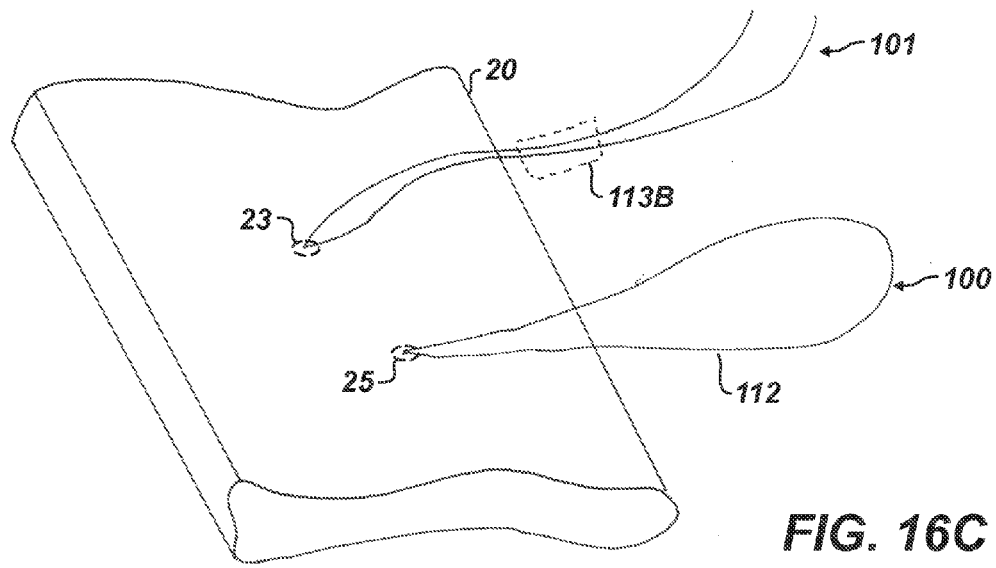
Figure 16D:
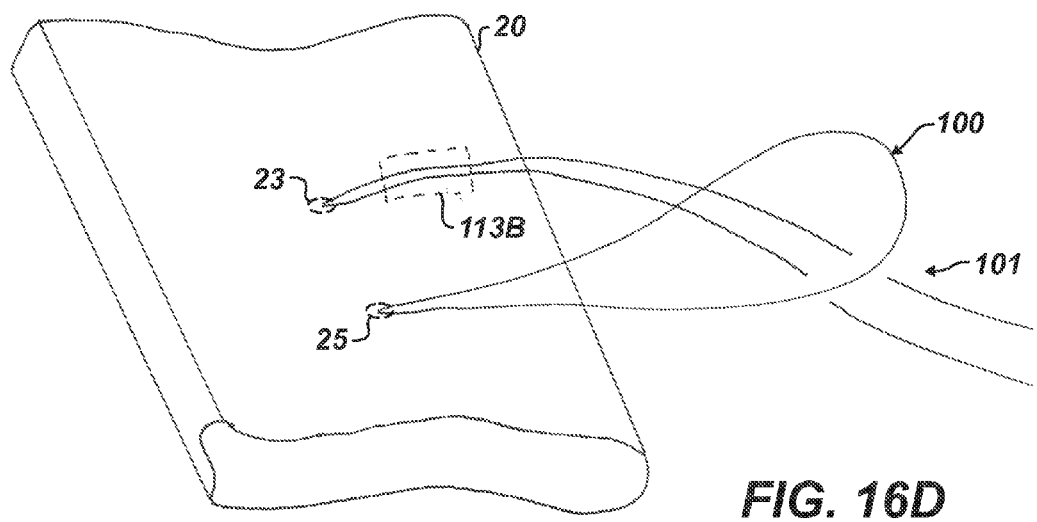

The free ends 103 of the shuttles 102A-B are pulled through the tendon 20 to bring the looped end 100 and the tail ends 101 through the suture points 25 and 23 as shown in FIG. 16C. Another rigid component 113B may then be positioned on the suture tails end 101 of the suture 112, and then the surgeon passes the tail ends 101 through the looped end 100, as shown in FIG. 16D. The stitch is pulled tight, and any fixing of the components 113A-B to the suture 112 can be performed, although as noted above the components 113A-B can be affixed to the suture 112 at any point in the procedure. Finally, the tail ends 101 affix to a bone fixation as discussed herein (e.g., FIGS. 23A-23B) to produce the reverse straight-line grip stitch as shown completed in FIG. 16A.

Figure 17A:
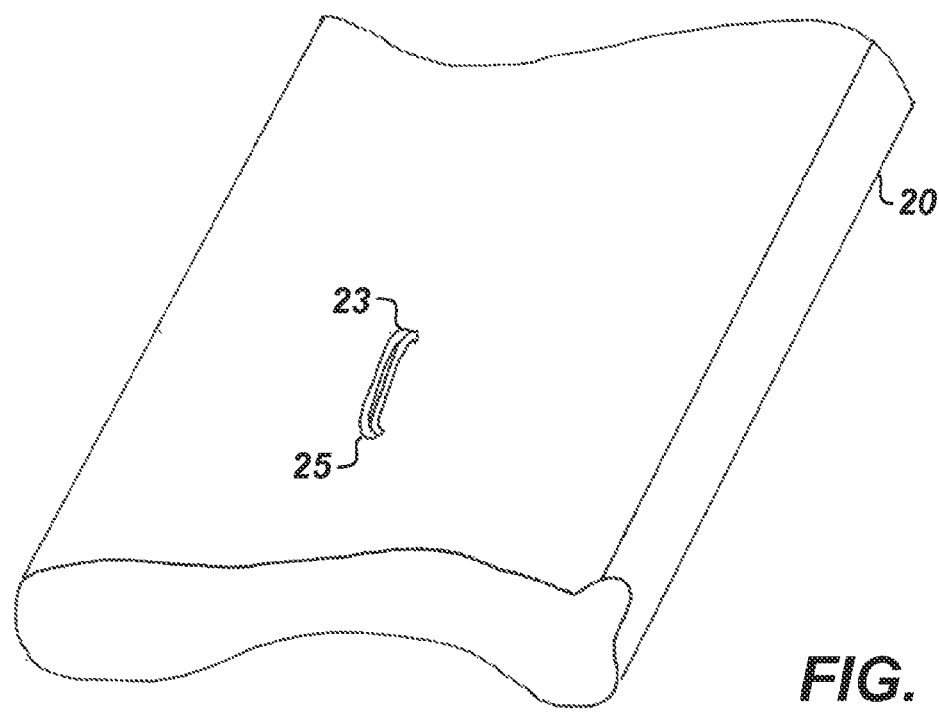
FIG. 17A shows the opposite side of the tendon as shown in FIGS. 15A and 16A showing the straight-line grip stitch or reverse straight-line grip stitch without a rigid component.
Figure 17B:
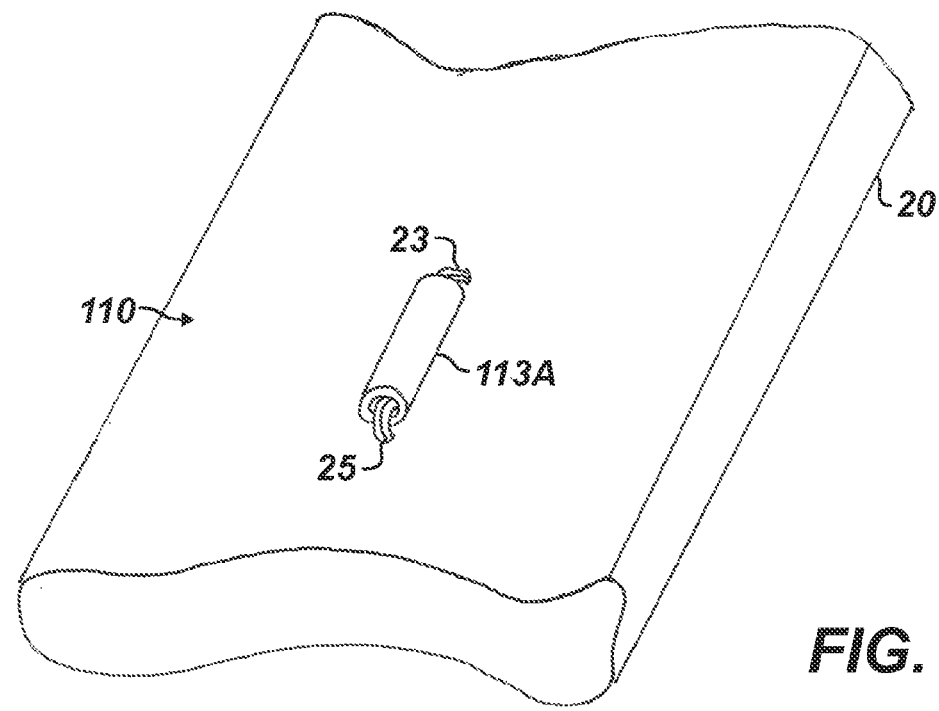
FIG. 17B shows the opposite side of the tendon as shown in FIGS. 15A and 16A showing the straight-line grip stitch or reverse straight-line grip stitch with a rigid component.

As noted above, the other side of the tendon 20 for the straight-line grip stitch or reverse straight-line grip stitch of FIGS. 15A and 16A may or may not use a rigid component 113A. For example, FIG. 17A shows the reverse side of the tendon 20 for either of these stitches when a rigid component is not used. By contrast, FIG. 17B shows the other side of the tendon 20 when the rigid component 113A is used for either the straight-line grip stitch or reverse straight-line grip stitch.

Like the grip stitch and knot tying grip stitch discussed above, these stitches of the straight-line grip stitch (FIG. 15A) and the reverse straight-line grip stitch (FIG. 16A) are expected to offer an improvement in strength and reduce suture pull through in the tendon compared to traditional techniques when the suture device 110 is used in conjunction with the stitch or when suture 112 is used alone in the stitch. The results of this will be appreciated with the benefit of the present disclosure.

Figure 18A:
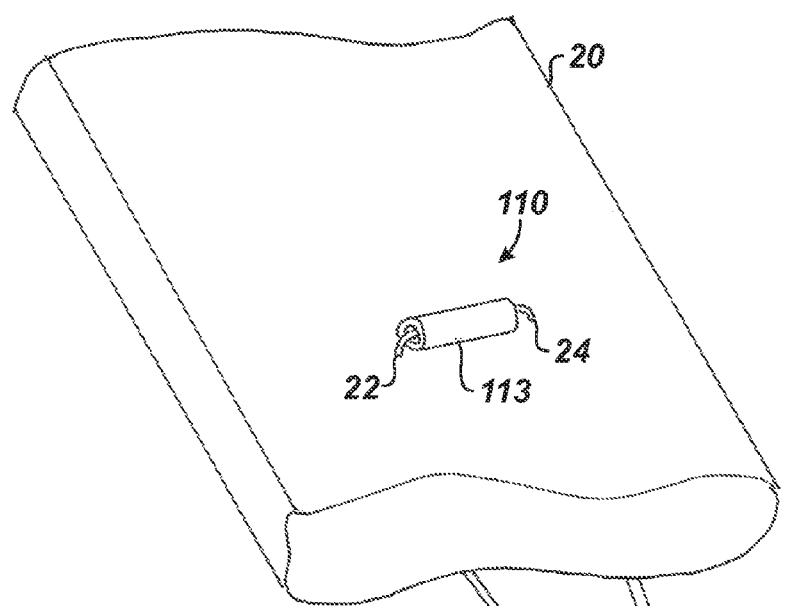
FIG. 18A shows a conventional horizontal mattress stitch using a segmentally rigid suture device of the present disclosure.
Figure 18B:
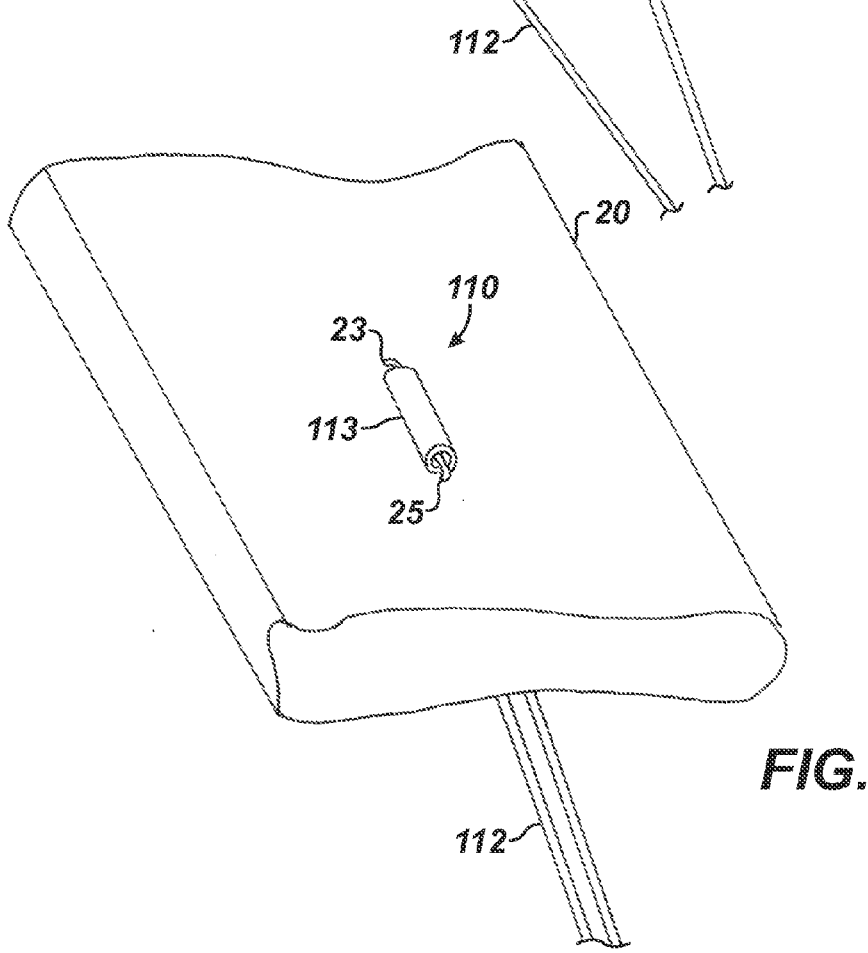
FIG. 18B shows a conventional vertical mattress stitch using a segmentally rigid suture device of the present disclosure.

As noted above, the segmentally rigid suture device 110 can be used with (and may enhance the effectiveness of) a massive cuff stitch, a vertical mattress stitch, a horizontal mattress stitch, a modified mason-allen, a simple stitch, a cinch stitch, a double-cinch stitch, or any other stitch configuration known and used in the art. As one example, FIGS. 18A-18B show how the device 110 can be used with conventional mattress stitches. In FIG. 18A, the mattress stitch is horizontal and has a rigid component 113 disposed on the suture 112 against the tendon 20 between the adjacent suture points 22 and 24. In FIG. 18B, the mattress stitch is vertical and has a rigid component 113 disposed on the suture 112 against the tendon 20 between the in-line suture points 23 and 25.

Figure 19A:
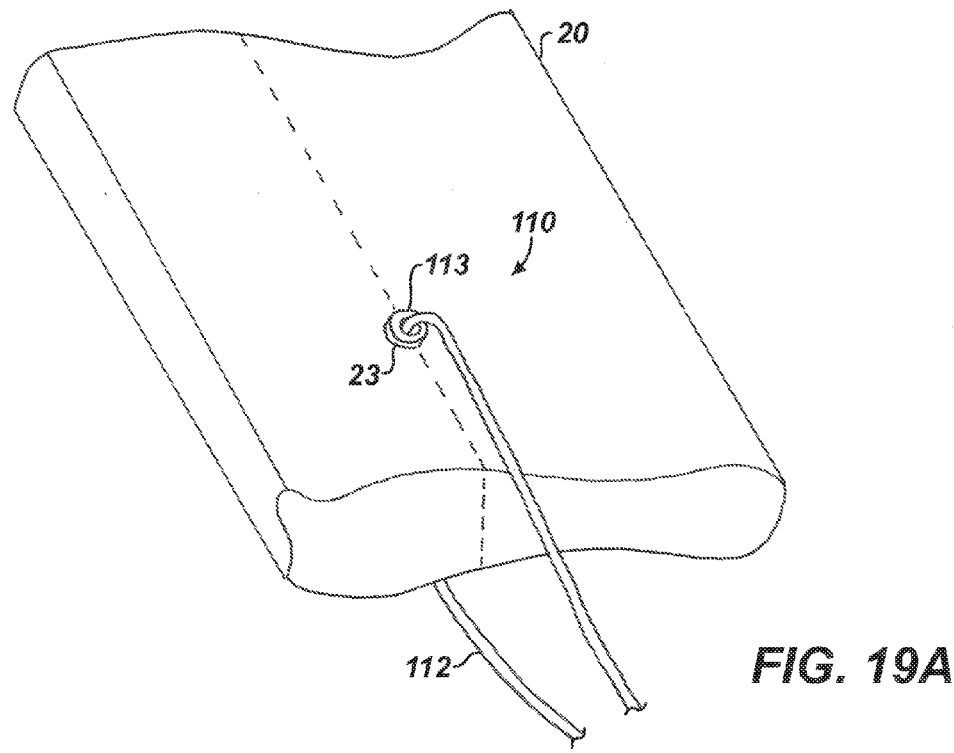
FIGS. 19A-19B show a conventional simple stitch using a segmentally rigid suture device of the present disclosure.
Figure 19B:
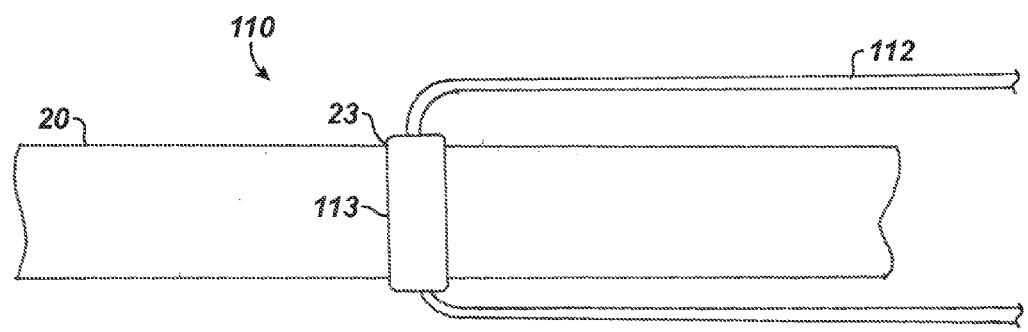

In FIGS. 19A-19B, a simple stitch is shown with a segmentally rigid suture device 110 of the present disclosure. Here, the rigid component 113 passes through a suture point 23 in the tendon 20 to limit compression on the tendon normal to the plane of the tendon caused by the suture 112.

Figure 20:
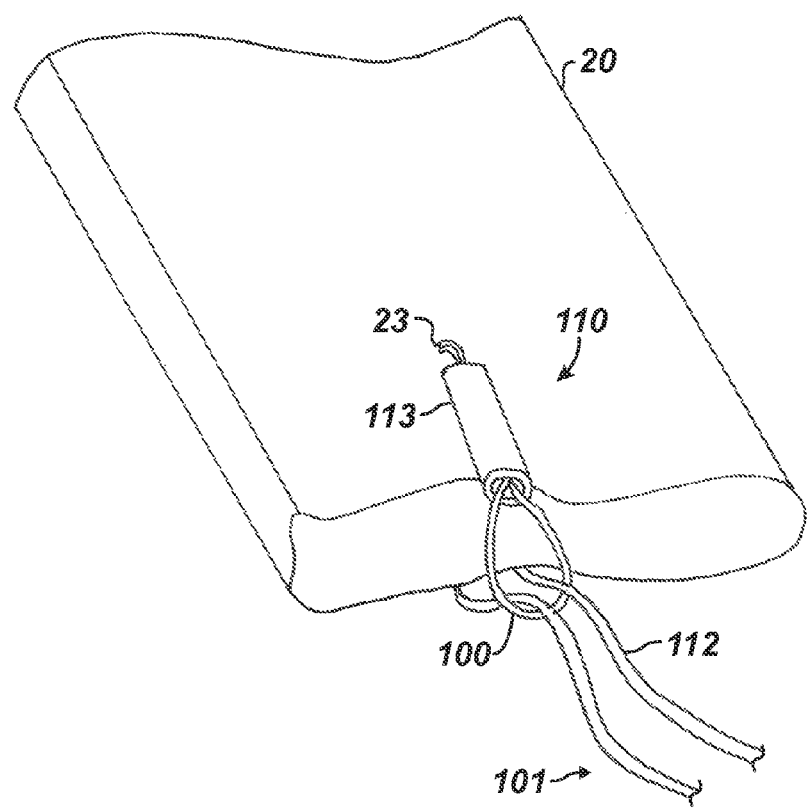
FIG. 20 shows a conventional cinch stitch using a segmentally rigid suture device of the present disclosure.

In FIG. 20, a cinch stitch is shown with a segmentally rigid suture device 110 of the present disclosure. This cinch stitch can be similar to the stitch disclosed in U.S. Pat. Pub. No. 2009/0036905. For this stitch, a looped end 100 of the suture 112 is passed through a suture point 23 in the tendon 20. A rigid component 113 positions on the looped end 100, and tail ends 101 of the suture 112 are passed through the looped end 100.

Figure 21A:
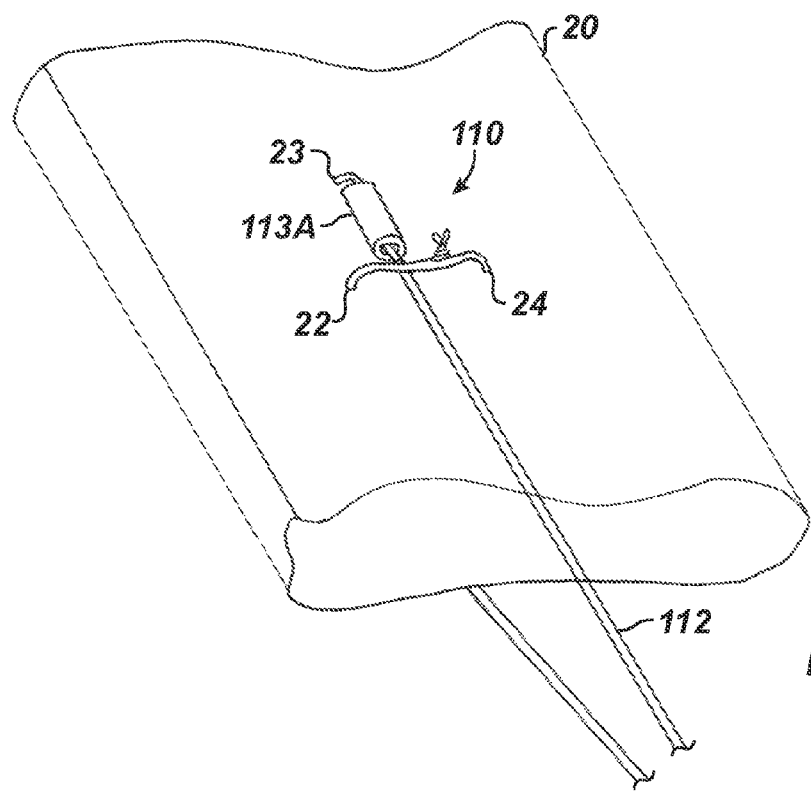
FIGS. 21A-21B show conventional massive cuff stitches using a segmentally rigid suture device of the present disclosure.
Figure 21B:
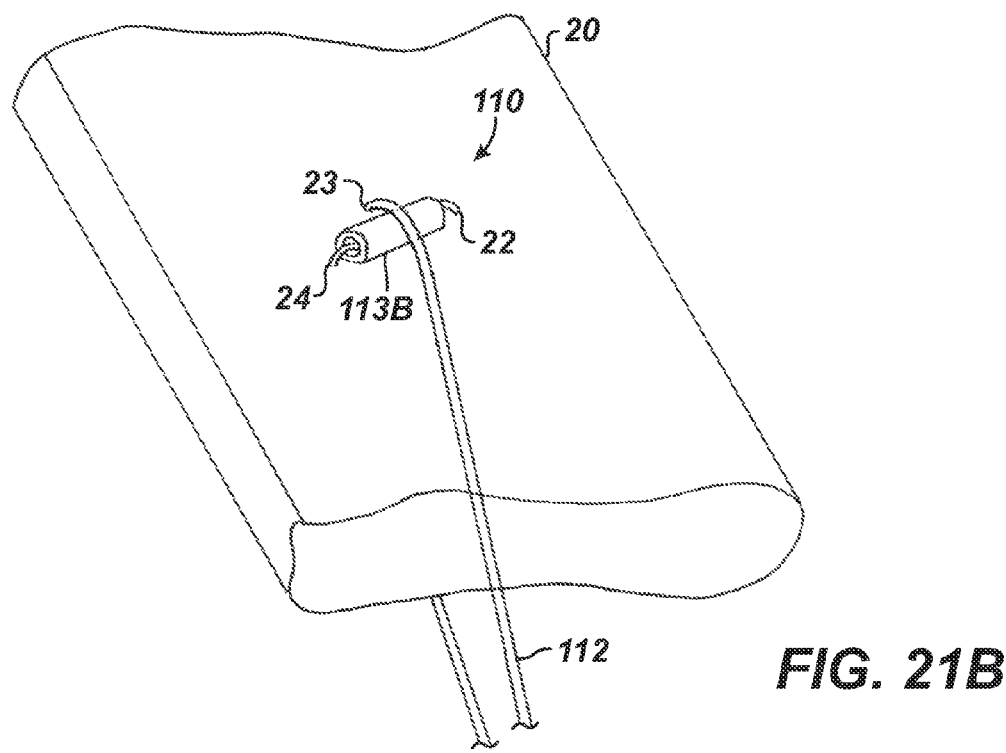

In FIGS. 21A-21B, two examples of a massive cuff stitch are shown with a segmentally rigid suture device 110 of the present disclosure. A first rigid component 113A is used on the simple stitch as shown in FIG. 21A. In a second embodiment, a rigid component 113B is used on the horizontal mattress stitch as shown in FIG. 21B. The horizontal mattress stitch is tied together on the other surface of the tendon 20. These two techniques may also be combined such that the mattress stitch contains a rigid component 113B on one side of the tendon 20 and the simple stitch contains a rigid component 113A on the opposite side of the tendon 20.

Figure 22A:
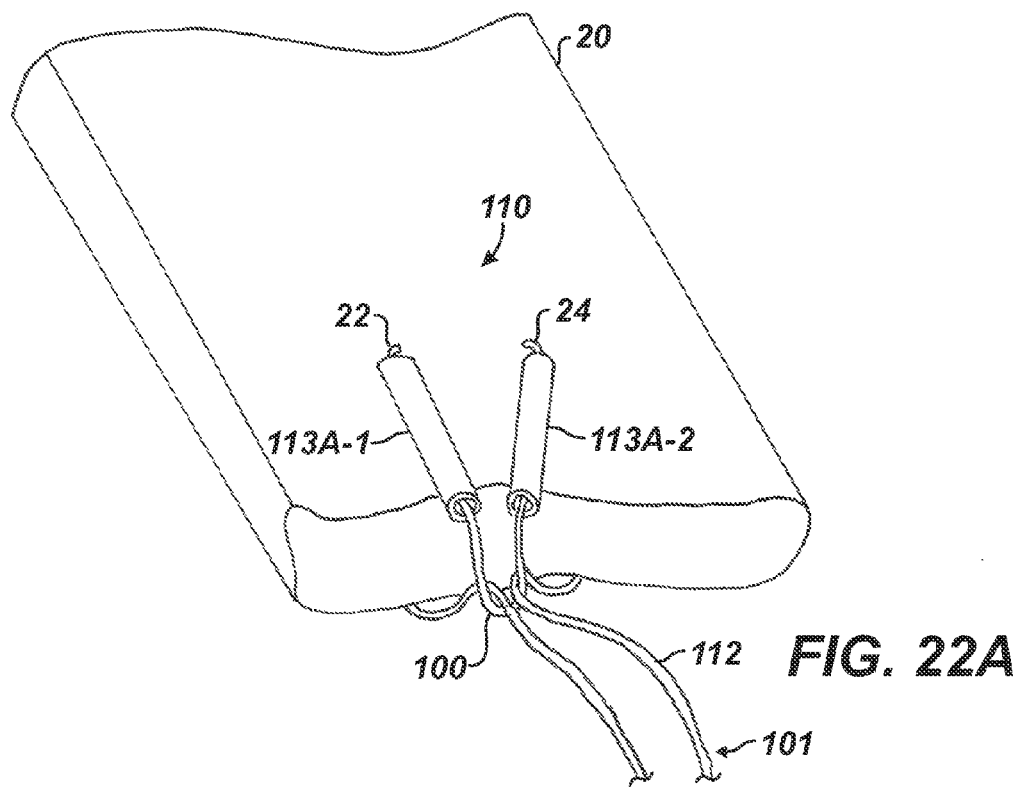
FIG. 22A shows a conventional double-cinch stitch using a segmentally rigid suture device according to the present disclosure.

Turning to FIG. 22A, a conventional double-cinch stitch is shown using a segmentally rigid suture device 110 according to the present disclosure. This stitch is similar to a stitch described in Ponce, B. A., et al., "Biomechanical Evaluation of 3 Arthroscopic Self-Cinching Stitches for Shoulder Arthroscopy: The Lasso-Loop, Lasso-Mattress, and Double-Cinch Stitches," The American Journal of Sports Medicine, available from http://ajs.sagepub.com/content/39/1/188, copyright 2011.

Figure 22B:
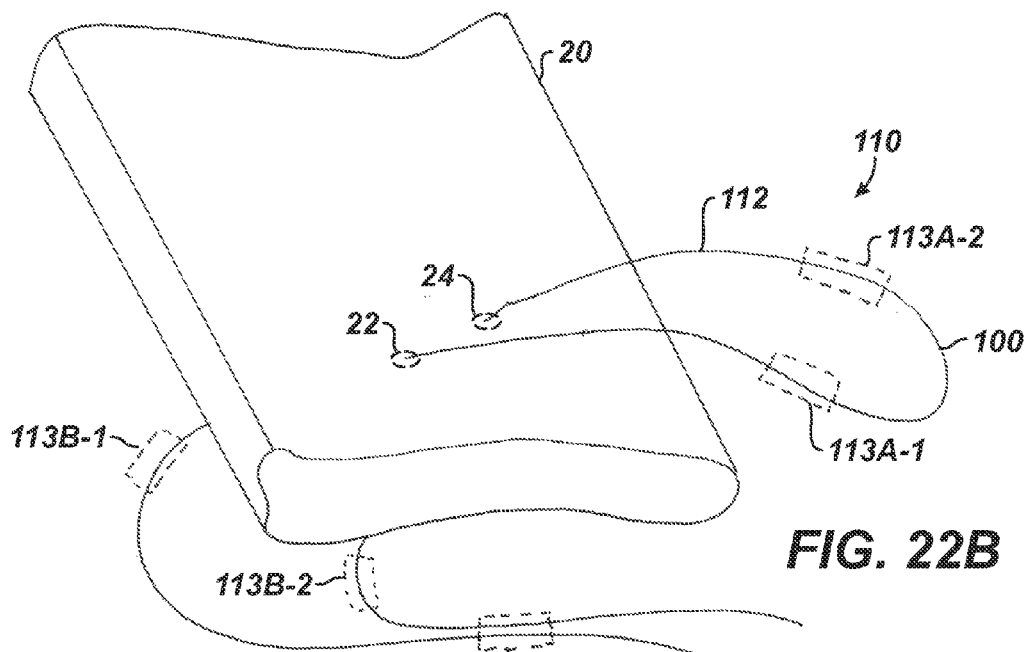
FIGS. 22B-22C shows steps for performing the conventional double-cinch stitch of FIG. 22A.

As shown in FIG. 22B, the suture device 110 can have rigid components 113A-1 and 113A-2 disposed near a central point of the device 110 where a loop 100 is to be formed. (These components 113A-1 and 113-A2 can be preassembled and fixed in place on the suture 112.) To make the stitch, the surgeon passes the tail ends 101 of the suture 112 through adjacent suture points 22 and 24 in the tendon 20. Separate rigid components 113B-1 and 113-B2 may be placed on each of the tail ends 101, or one rigid component 113C may be placed on both of the tail ends 101. As one example, these rigid components 113B-1, B-2, and C can be external elements similar to 114 in FIG. 6A that the surgeon can slide in place on the suture 112, and they can be crimped in place on the suture 112 after the suture 112 is pulled tight in completing the stitch. Alternatively, the two rigid components 113B-1 and B-2, if sufficiently "thin" relative to the suture 112, can actually be preassembled in place on the suture 112 and passed through the tendon 20 when the surgeon makes the stitches through the suture points 22 and 24. These and other possibilities disclosed herein will be appreciated by one skilled in the art.

Figure 22C:
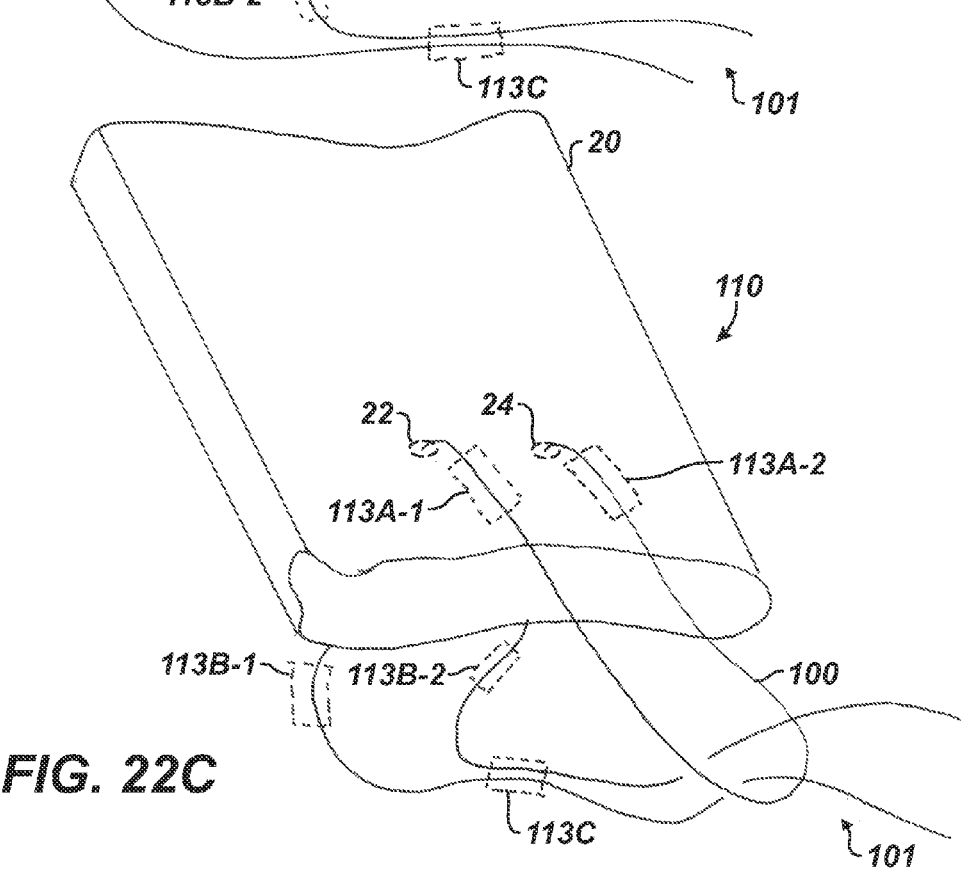

As then shown in FIG. 22C, the surgeon passes the tail ends 101 through the loop 100 formed in the device 110, and the stitch is pulled tight. If any of the rigid components 113 need to be fixed in place on the suture 112, the surgeon can perform any crimping or the like at this point. Finally, the tail ends 101 affix to a bone fixation as discussed herein to produce the double-cinch stitch as shown completed in FIG. 22A.

Figure 23A:
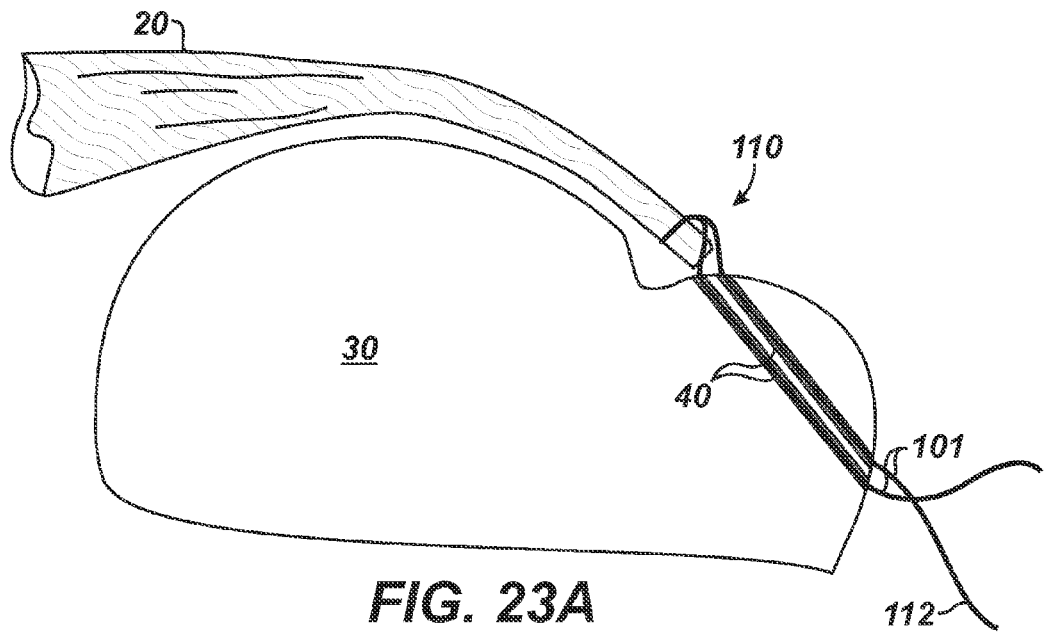
FIGS. 23A-23B show two techniques for affixing tendon to bone using suture.
Figure 23B:
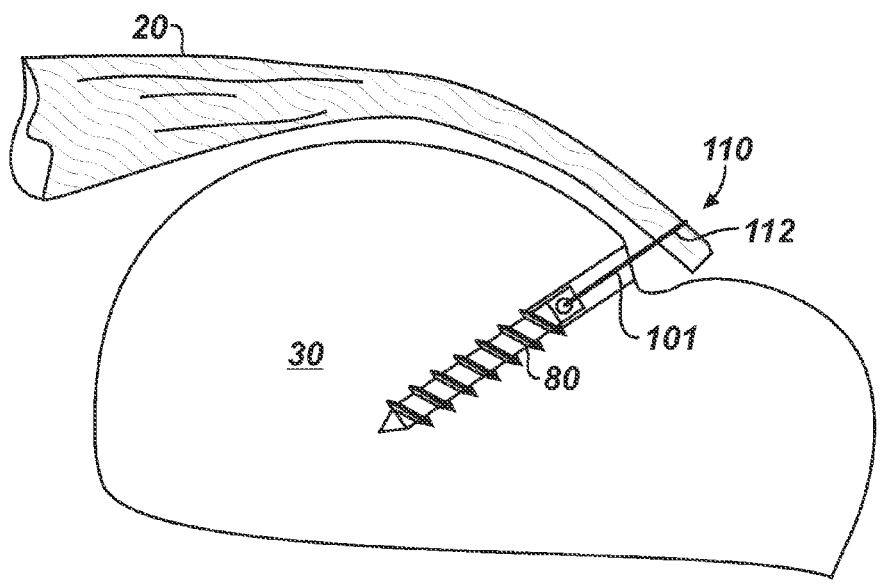

FIGS. 23A-23B show two techniques for affixing the suture of the stitches disclosed herein to bone. In FIG. 23A, bone tunnels 40 are formed in bone 30, and tail ends 101 to the device's suture 112 pass through the tunnels 40 to be tied together opposite the tendon 20 and stitch. In FIG. 23B, a bone screw 80 is disposed in bone and has the tail ends 101 of the device's suture 112 affixed thereto. These and other techniques for affixing suture to bone can be used as will be appreciated with the benefit of the present disclosure.

As noted above, the grip stitch and knot-tying grip stitch offer advantages over the prior art when a segmentally rigid suture device 110 is used or even when only suture is used. To help illustrate the advantages, discussion turns to the graphs in FIGS. 24-26.

Figure 24:
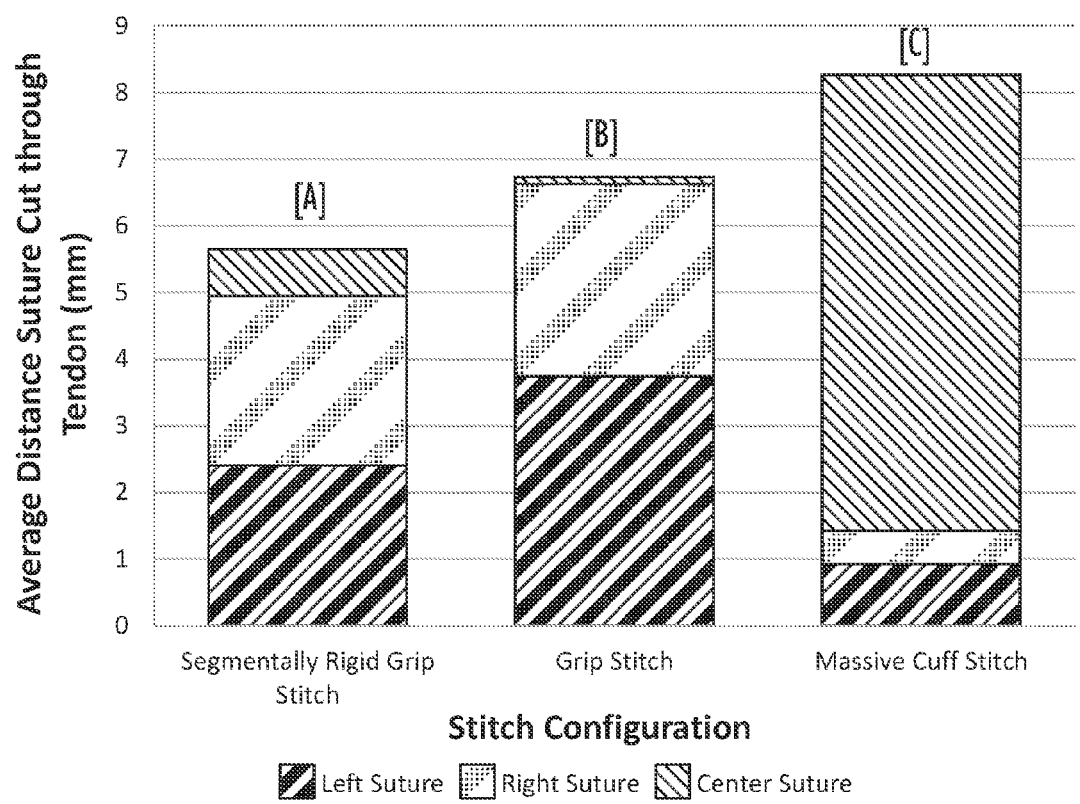
FIG. 24 graphs an average distance that suture cuts through an infraspinatus tendon of sheep using various stitch configurations during cyclical and pull-to-failure testing.

FIG. 24 graphs an average distance that suture cuts through an infraspinatus tendon of sheep using various stitch configurations during cyclical and pull-to-failure testing.

The graph compares three stitch configurations: (A) the grip stitch using a segmentally rigid suture device, (B) the grip stitch using conventional suture, and (C) the massive cuff stitch of the prior art. A comparison of the average distance for each suture point (left, center, and right) for the three configurations is shown. Table 1 below provides numerical values for the testing performed.

TABLE 1

| Configuration | Left Pull Thru (mm) | Right Pull Thru (mm) | Center Pull Thru (mm) | Total Pull Thru (mm) |
|---|---|---|---|---|
| (A) Segmentally Rigid Grip Stitch | 2.4 | 2.55 | 0.7 | 5.64 |
| (B) Grip Stitch | 3.74 | 2.89 | 0.11 | 6.74 |
| (C) Massive Cuff Stitch | 0.92 | 0.5 | 6.85 | 8.27 |

As can be seen, the grip stitch using conventional suture (B) offers an improvement over the prior art massive cuff stitch (C), and the grip stitch using a segmentally rigid suture device (A) offers the best improvement by reducing the average distance suture cuts though tendon during the cyclical and pull-to-failure testing.

Figure 25:
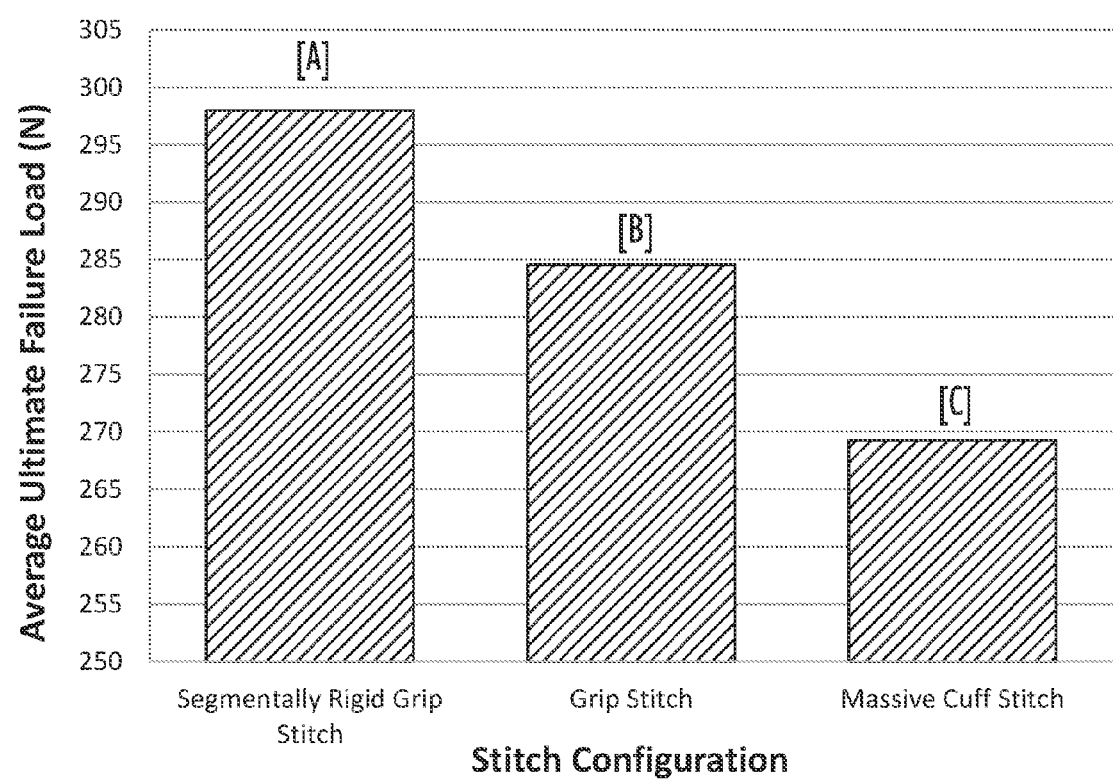
FIG. 25 graphs an average ultimate failure load of various stitch configurations during pull-to-failure testing on an infraspinatus tendon of sheep.

FIG. 25 graphs an average ultimate failure load of various stitch configurations during pull-to-failure testing on an infraspinatus tendon of sheep. Again, the graph compares three stitch configurations: (A) the grip stitch using a segmentally rigid suture device, (B) the grip stitch using conventional suture, and (C) the massive cuff stitch of the prior art. Table 2 below provides numerical values for the testing performed.

TABLE 2

| Configuration | Average Ultimate Failure Load (N) |
|---|---|
| (A) Segmentally Rigid Grip Stitch | 297.938 |
| (B) Grip Stitch | 284.571 |
| (C) Massive Cuff Stitch | 269.250 |

As can be seen, the grip stitch using conventional suture (B) offers an improvement over the prior art massive cuff stitch (C), and the grip stitch using a segmentally rigid suture device (A) offers the best improvement by increasing the average failure load.

Figure 26:
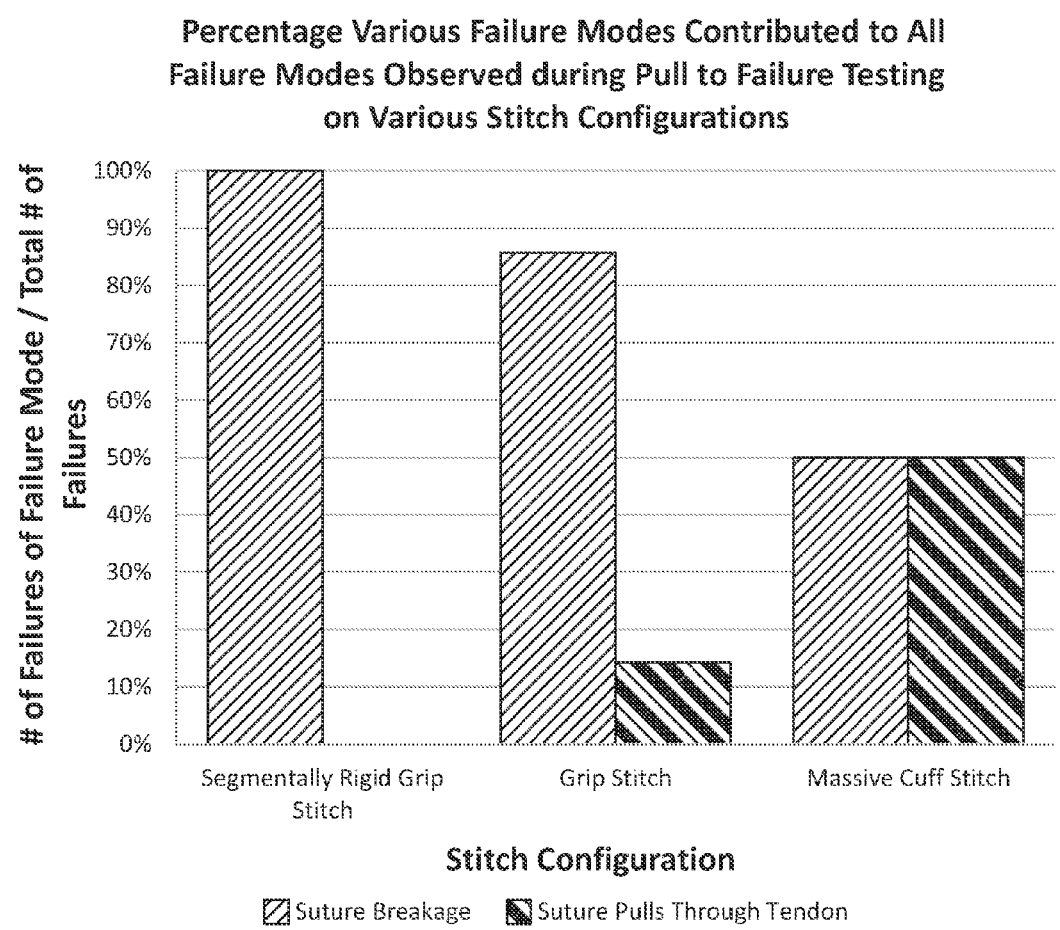
FIG. 26 graphs a percentage of various failure modes contributing to all failure modes observed during pull-to-failure testing on various stitch configurations.

FIG. 26 graphs a percentage of various failure modes contributing to all failure modes observed during pull-to-failure testing on various stitch configurations. Again, the graph compares three stitch configurations: (A) the grip stitch using a segmentally rigid suture device, (B) the grip stitch using conventional suture, and (C) the massive cuff stitch of the prior art. As can be seen, the massive cuff stitch of the prior art (C) failed 50% of the time due to suture breakage and failed 50% of the time by suture pulling through the test tendon. Table 3 below provides numerical values for the testing performed.

TABLE 3

| Configuration | Suture Break | Suture Pull Thru Tendon | % of Failure due to Suture Break | % of Failure due to Suture Pull Thru Tendon |
|---|---|---|---|---|
| (A) Segmentally Rigid Grip Stitch | 8 | 0 | 100% | 0% |
| (B) Grip Stitch | 6 | 1 | 86% | 14% |
| (C) Massive Cuff Stitch | 3 | 3 | 50% | 50% |

As can be seen, the grip stitch using conventional suture (B) offers an improvement because it failed about 85% of the time due to suture breakage and only pulled through the test tendon about 15% of the time. Finally, the grip stitch using a segmentally rigid suture device (A) showed failure due to suture breakage only and did not pull through the test tendon.

As these graphs in FIGS. 24-26 indicate, the grip stitch using a segmentally rigid suture device (A) and the grip stitch using conventional suture (B) can resist failure up to higher loads than the prior art massive cuff stitch (C). Moreover, the grip stitch using a segmentally rigid suture device (A) and the grip stitch using conventional suture (B) tend to fail by suture breakage rather than pulling through the tendon, which can cause further complications. Although not reflected in the tables and graphs, initial testing has also shown that a grip stitch using suture with a central portion formed from a thicker suture section (configured and stitched much like depicted in FIG. 14B) as opposed to a more rigid material performed less favorably and may not be preferred over other embodiments of the device 110.

The foregoing description of preferred and other embodiments is not intended to limit or restrict the scope or applicability of the inventive concepts conceived of by the Applicants. It will be appreciated with the benefit of the present disclosure that features described above in accordance with any embodiment or aspect of the disclosed subject matter can be utilized, either alone or in combination, with any other described feature, in any other embodiment or aspect of the disclosed subject matter.

As will also be appreciated, the suture techniques disclosed herein may be performed using arthroscopic or open surgery and certain arthroscopic steps can be performed intracorporeally or extracorporeally. These and other general details related to surgery to repair soft tissue are omitted as they would be apparent to one skilled in the art. As will further be appreciated, any of the segmentally rigid suture devices 110 disclosed herein and any of the rigid components 113 disclosed herein can be used with any of the various stitching techniques discussed herein or with those of the prior art. Moreover, a given suture device 110 may use one or more different types of the rigid components 113 thereon as suits the particular stitch and implementation. Finally, reference to suture herein can refer to a continuous length of suture or separate sections of suture that are interconnected together, tied end-to-end, or otherwise associated with one another as "suture."

What is claimed is:

1. A suture device for affixing soft tissue with a stitch having at least one suture pass into the soft tissue, the device comprising:
   a suture composed of a suture material; and
   at least one segment disposed on the suture and composed of a second material, the at least one segment being at least longitudinally rigid, the at least one segment embedded in an external portion of the suture passing over an exterior of the at least one segment, the at least one segment affixed to an internal portion of the suture passing through the at least one segment, the suture comprising at least one retention feature disposed on a length of the suture, the at least one retention feature limiting a position of the at least one segment on the length of the suture, the at least one segment configured to be disposed adjacent an outside surface of the soft tissue in the stitch adjacent the at least one suture pass, the at least one segment configured to support the suture device against the outside surface of the soft tissue and a compressive load on the soft tissue by the suture at the at least one suture pass.

2. The device of claim 1, wherein the second material of the at least one segment is the same as the suture material.

3. The device of claim 1, wherein the second material comprises metal, titanium, plastic, polyethylene, thermoplastic, an orthopedic plastic, polyoxymethylene, polyether ether ketone, bioabsorbable material, biologic material, allograft bone, ceramic, or a combination thereof.

4. The device of claim 1, wherein the at least one segment defines an internal passage through which at least a portion of the suture material passes.

5. The device of claim 4, wherein the at least one segment crimps onto the portion of the suture material passing through the internal passage.

6. The device of claim 1, wherein the external portion of the suture material of the suture surrounds the at least one segment.

7. The device of claim 1, wherein the stitch has at least two passes into the soft tissue; wherein the at least one segment is disposed adjacent the outside surface of the soft tissue in the stitch between the at least two suture passes; and wherein the at least one segment supports the suture device against the outside surface of the soft tissue and limits the compressive load on the soft tissue by the suture between the at least two suture passes.

8. The device of claim 7, wherein to limit the compressive load on the soft tissue, the at least one segment limits a first portion of the suture for a first of the at least two suture passes at a first end of the at least one segment from moving toward a second portion of the suture for a second of the at least two suture passes at a second end of the at least one segment.

9. The device of claim 1, wherein at least a portion of the suture in the stitch is disposed against the at least one segment; and wherein the at least one segment limits movement of the portion of the suture against the soft tissue.

10. The device of claim 1, wherein the at least one segment comprises a first segment disposed at a first point on the suture and a second segment disposed at a second point on the suture, the first and second segments separated by a length of the suture.

11. The suture device of claim 1, wherein the internal portion of the suture comprises a core of the suture; and wherein the external portion of the suture comprises a sheath of the suture disposed about the core.

12. The suture device of claim 1, wherein the at least one retention feature disposed on the internal portion of the suture is engageable against an internal passage of the at least one segment through which the internal portion of the suture passes.

13. The suture device of claim 1, wherein the at least one retention feature comprises a loop formed in the internal portion of the suture and passing through an internal passage and around the exterior of the at least one segment.

14. A method of repairing soft tissue, comprising:
providing a suture device having a suture and at least one segment, the suture composed of a suture material, the at least one segment composed of a second material and being at least longitudinally rigid, the at least one segment embedded in an external portion of the suture passing over an exterior of the at least one segment and affixed to an internal portion of the suture passing through the at least one segment, the suture comprising at least one retention feature disposed on a length of the suture, the at least one retention feature limiting a position of the at least one segment on the length of the suture;

forming a loop with the suture device by passing the suture through the soft tissue at first suture points;

passing at least one end of the suture through the soft tissue at a second suture point;

passing the at least one end of the suture through the formed loop; and limiting a compressive load on the soft tissue by the suture between at least one of the first suture points and the second suture point by positioning the at least one segment disposed on the suture device against an outside surface of at least one side of the soft tissue between the first and second suture points.

15. The method of claim 14, wherein passing the suture through the soft tissue at the first suture points comprises passing the at least one end of the suture through the soft tissue.

16. The method of claim 14, wherein positioning the at least one segment disposed on the suture device against the outside surface of the at least one side of the soft tissue between the first and second suture points comprises:
adding the at least one segment in place on the suture of the suture device; or
having the at least one segment already added in place on the suture of the suture device.

17. The method of claim 14, wherein passing the at least one end of the suture device through the soft tissue at the second suture point comprises passing both of the ends of the suture through the soft tissue at one or more of the second suture point; and wherein passing the at least one end of the suture through the formed loop comprises passing both of the ends of the suture through the formed loop.

18. The method claim 17, wherein passing both of the ends of the suture through the soft tissue comprises using a suture shuttling device to pass the suture.

19. The method of claim 17, wherein the suture device has first and second segments of the at least one segment; and wherein limiting the compressive load comprises limiting the compressive load on the soft tissue by the suture between both of the first suture points and the one or more second suture points by positioning the first and second segments disposed on the suture device against the outside surface of the at least one side of the soft tissue between the first and second suture points.

20. The method of claim 17, wherein the suture device has first and second segments of the at least one segment; and wherein limiting the compressive load comprises:
limiting the compressive load on the soft tissue by the suture between the first suture point and the one or more second suture points by positioning the first segment disposed on the suture device against the outside surface of a first of the at least one side of the soft tissue between the first and second suture points; and limiting the compressive load on the soft tissue by the suture between the first suture point and the one or more second suture points by positioning the second segment disposed on the suture device against the outside surface of a second of the at least one side of the soft tissue between the first and second suture points.

21. The method of claim 17, further comprising:
passing at least a portion of the suture in the stitch over the at least one segment; and
limiting movement of the portion of the suture against the soft tissue with the at least one segment.

22. The method of claim 14, further comprising affixing the suture to bone.

23. A method of repairing soft tissue, comprising:
providing a suture device having a suture and at least one segment, the suture composed of a suture material, the at least one segment composed of a second material and being at least longitudinally rigid, the at least one segment embedded in an external portion of the suture passing over an exterior of the at least one segment and affixed to an internal portion of the suture passing through the at least one segment, the suture comprising at least one retention feature disposed on a length of the suture, the at least one retention feature limiting a position of the at least one segment on the length of the suture;
forming a loop with the suture by passing ends of the suture through soft tissue at one or more first suture points;
passing the ends of the suture through the formed loop; and
limiting a compressive load on the soft tissue by the suture between the one or more first suture points and the formed loop by positioning the at least one segment disposed on the suture device against an outside surface of at least one side of the soft tissue between the one or more first suture points and the formed loop.

24. The method claim 23, wherein passing the ends of the suture through the soft tissue comprises using a suture shuttling device to pass the suture.

25. The method of claim 23, further comprising:
passing the ends of the suture through the soft tissue at one or more second suture points before passing the ends of the suture through the formed loop;
wherein limiting the compressive load comprises limiting the compressive load on the soft tissue by the suture between the first and second suture points by positioning the at least one segment disposed on the suture device against the outside surface of the at least one side of the soft tissue between the first and second suture points.

26. The method of claim 25, wherein the suture device has first and second of the at least one segment; and wherein limiting the compressive load comprises:
limiting the compressive load on the soft tissue by the suture between the first suture point and the one or more second suture points by positioning the first segment disposed on the suture device against the outside surface of a first of the at least one side of the soft tissue between the first and second suture points; and limiting the compressive load on the soft tissue by the suture between the first suture point and the one or more second suture points by positioning the second segment disposed on the suture device against the outside surface of a second of the at least one side of the soft tissue between the first and second suture points.

27. A method of repairing soft tissue, comprising:
providing a suture device having a suture and at least one segment, the suture composed of a suture material, the at least one segment composed of a second material and being at least longitudinally rigid, the at least one segment embedded in an external portion of the suture passing over an exterior of the at least one segment and affixed to an internal portion of the suture passing through the at least one segment, the suture comprising at least one retention feature disposed on a length of the suture, the at least one retention feature limiting a position of the at least one segment on the length of the suture;
passing ends of the suture through the soft tissue at first and second suture points; and
limiting a compressive load on the soft tissue by the suture between the first and second suture points by positioning the at least one segment disposed on the suture device against an outside surface of at least one side of the soft tissue between the first and second suture points.

28. A method of repairing soft tissue, comprising:
providing a suture device having a suture and at least one segment, the suture composed of a suture material, the at least one segment composed of a second material and being at least longitudinally rigid, the at least one segment embedded in an external portion of the suture passing over an exterior of the at least one segment and affixed to an internal portion of the suture passing through the at least one segment the suture comprising at least one retention feature disposed on a length of the suture, the at least one retention feature limiting a position of the at least one segment on the length of the suture;
making a simple stitch in soft tissue at a first suture point with the suture,
making a mattress stitch through the soft tissue at second and third suture points with a separate suture piece tied over the suture from the simple stitch; and
limiting a compressive load on the soft tissue by the suture between the first suture point and the mattress stitch by positioning the at least one segment disposed on the suture device against an outside surface of at least one side of the soft tissue between the first suture point and the mattress stitch.

29. The method of claim 28, wherein the separate suture piece comprises another suture device having a suture and at least one other segment, the method further comprising:
limiting another compressive load on the soft tissue by the separate suture piece between the second and third suture points by positioning the other at least one segment of the other suture device against an outside surface of another side of the soft tissue between the second and third suture points.

* * * * *